US006552006B2

(12) United States Patent
Raz et al.

(10) Patent No.: US 6,552,006 B2
(45) Date of Patent: Apr. 22, 2003

(54) IMMUNOMODULATORY POLYNUCLEOTIDES IN TREATMENT OF AN INFECTION BY AN INTRACELLULAR PATHOGEN

(75) Inventors: Eyal Raz, Del Mar, CA (US); Richard Kornbluth, La Jolla, CA (US); Antonio Catanzaro, San Diego, CA (US); Tomoko Hayashi, San Diego, CA (US); Dennis Carson, Del Mar, CA (US)

(73) Assignees: The Regents of the University of California, Oakland, CA (US); The United States of America as represented by the Department of Veteran Affairs, Washington, DC (US)

( * ) Notice: Subject to any disclaimer, the term of this patent is extended or adjusted under 35 U.S.C. 154(b) by 32 days.

(21) Appl. No.: 09/774,403

(22) Filed: Jan. 30, 2001

(65) Prior Publication Data

US 2002/0086295 A1 Jul. 4, 2002

Related U.S. Application Data

(60) Provisional application No. 60/179,353, filed on Jan. 31, 2000.

(51) Int. Cl.$^7$ ................................................ A61P 37/06

(52) U.S. Cl. ...................... 514/44; 435/320.1; 536/23.1

(58) Field of Search ..................... 514/44; 435/320.1; 536/23.1

(56) References Cited

U.S. PATENT DOCUMENTS

| | | | |
|---|---|---|---|
| 5,736,524 A | 4/1998 | Content et al. | |
| 6,194,388 B1 | 2/2001 | Krieg et al. | |
| 6,207,646 B1 | 3/2001 | Krieg et al. | |
| 6,214,806 B1 | 4/2001 | Krieg et al. | |
| 6,218,371 B1 | 4/2001 | Krieg et al. | |
| 6,228,371 B1 | 5/2001 | Nano et al. | |
| 6,239,116 B1 | 5/2001 | Krieg et al. | |

FOREIGN PATENT DOCUMENTS

| | | |
|---|---|---|
| WO | WO 97/28259 | 7/1997 |
| WO | WO 99/11275 | 11/1999 |
| WO | WO 99/56755 | 11/1999 |
| WO | WO 00/20039 | 4/2000 |
| WO | WO 01/22972 A2 | 4/2001 |
| WO | WO 01/22990 A2 | 4/2001 |

OTHER PUBLICATIONS

Verma et al., Gene therapy–promises, problems and prospects, 1997, Nature, vol. 389, pp. 239–242.*
Marshall, Gene therapy's growing pains, 1995, Science, vol. 269, pp. 1050–1055.*
Mountain, Gene therapy: the first decade, 2000, TIBTECH, vol. 18, pp. 119–128.*
Romano et al., Latest developments in gene transfer technology: Achievements, perspectives and controversies over therapeutic applications, 2000, Stem Cells, vol. 18, pp. 19–39.*
Krieg, Direct immunologic activities of CpG DNA and implications for gene therapy, 1999, The Journal of Gene Medicine, vol. 1, pp. 56–63.*
Tokunaga et al., How BCG to the discovery of immuno-stimulatory DNA, 1999, Japan J. Infect. Dis., vol. 52, pp. 1–11.*
Orkin et al., Report and recommendations of the panel to assess the NIH investment in research on gene therapy, 1995, NIH,pp. 1–33.*
Kmiec, Gene therapy, 1999, American Scientist, vol. 87, pp. 240–247.*
Appelberg et al. (1994) "Role of Gamma Inferferon and Tumor Necrosis Factor Alpha during T–Cell–Independent and –Dependent Phases of Mycobacterium avium Infection." *Infection and Immunity*, vol. 62(9):3962–3971.
Autran et al. (1997) "Positive Effects of Combined Antiretroviral Therapy on CD4+ T Cell Homeostasis and Function in Advanced HIV Disease." *Science*, vol. 277:112–116.
Bermudez et al. (1991) "Interaction of *Mycobacterium avium* Complex with Human Macrophages: Roles of Membrane Receptors and Serum Proteins." *Infection and Immunity*, vol. 59(5):1697–1702.
Bonato et al. (1998) "Identification and Characterization of Protective T Cells and hsp65 DNA–Vaccinated and *Mycobacterium tuberculosis*–Infected Mice." *Infection and Immunity*, vol. 66(1):169–175.
Chin et al. (1994) "The Impact of *Mycobacterium avium* Complex Bacteremia and Its Treatment on Survival of AIDS Patients—A Prospective Study." *The Journal of Infectious Diseases*, vol. 170:578–84.
Crowe et al. (1991) "Predictive Value of CD4 Lymphocyte Numbers for the Development of Opportunistic Infections and Malignancies in HIV–Infected Persons." *Journal of Acquired Immune Deficiency Syndromes*, vol. 4:770–776.
Doherty et al. (1997) "Defects in Cell–Mediated Immunity Affect Chronic, but Not Innate, Resistance of Mice to *Mycobacterium avium* Infection." *Journal of Immunology*, vol. 158:4822–4831.
Doherty et al. (1998) "IL–12 Promotes Drug–Induced Clearance of *Mycobacterium avium* Infection in Mice." *Journal of Immunology*, vol. 160:5428–5435.

(List continued on next page.)

Primary Examiner—James Ketter
Assistant Examiner—Daniel M. Sullivan
(74) Attorney, Agent, or Firm—Carol L. Francis; Paula A. Borden; Bozicevic, Field & Francis, LLP

(57) ABSTRACT

The present invention features methods for treatment or prevention of infection by intracellular pathogens (e.g., Mycobacterium species) by administration of an immunomodulatory nucleic acid molecule. In one embodiment, immunomodulatory nucleic acid molecule are administered in combination with another anti-pathogenic agent to provide a synergistic anti-pathogenic effect.

43 Claims, 8 Drawing Sheets

OTHER PUBLICATIONS

Edwards et al. (1986) "The Immunology of Mycobacterial Diseases." *Am. Rev. Respir. Dis.*, vol. 134:1062–1071.

Faria et al. (2001) "Phosphoroamidate oligonucleotides as potent antisense molecules in cells and in vivo." *Nature Biotechnology*, vol. 19:40–44.

Fattorini et al. (1994) "Induction of IL–1β, IL–6, TNF–α, GM–CSF and G–CSF in human macrophages by smooth transparent and smooth opaque colonial variants of *Mycobacterium avium*." *J. Med. Microbiol.*, vol. 40:129–133.

Halpern et al. (1996) "Bacterial DNA Induces Murine Interferon–γ Production of Stimulation of Interleukin–12 and Tumor Necrosis Factor–α." *Cellular Immunology*, vol. 167:72–78.

Holland et al. (1994) "Treatment of Refractory Disseminated Nontuberculous Mycobacterial Infection with Interferon Gamma." *The New England Journal of Medicine*, vol. 330(19):1348–1355.

Horsburgh et al. (1991) "Mycobacterium Avium Complex Infection in the Acquired Immunodeficiency Syndrome." *The New England Journal of Medicine*, vol. 324(19):1332–1338.

Kamath et al. (1999) "Differential Protective Efficacy of DNA Vaccines Expressing Secreted Proteins of *Mycobacterium tuberculosis*." *Infection and Immunity*, vol. 67(4):1702–1707.

Klinman et al. (1996) "CpG motifs present in bacterial DNA rapidly induce lymphocytes to secrete interleukin 6, interleukin 12, and interferon γ." *Proc. Natl. Acad. Sci. USA*, vol. 93:2879–2883.

Klinman et al. (1999) "Repeated Administration of Synthetic Oligodeoxynucleotides Expressing CpG Motifs Provides Long–Term Protection against Bacterial Infection." *Infection and Immunity*, vol. 67(11):5658–5663.

Kobayashi et al. (1995) "Protection of Mice from *Mycobacterium avium* Infection by Recombinant Interleukin–12." *Antimicrobial Agents and Chemotherapy*, vol. 39(6):1369–1371.

Krieg et al. (1995) "CpG motifs in bacterial DNA trigger direct B–cell activation." *Nature*, vol. 374:546–549.

Krieg et al. (1998) "CpG DNA Induces Sustained IL–12 Expression In Vivo and Resistance to Listeria monocytogenes Challenge." *Journal of Immunology*, vol. 161:2428–2434.

Martin–Orozco et al. (1999) "Enhancement of antigen–presenting cell surface molecules involved in cognate interactions by immunostimulatory DNA sequences." *International Immunology*, vol. 11(7):111–1118.

Masur (1993) "Recommendations on Prophylaxis and Therapy for Disseminated *Mycobacterium avium* Complex Disease in Patients Infected with the Human Immunodeficiency Virus." *New. Eng. J. Med.*, vol. 329:898–904.

Messina et al. (1991) "Stimulation of In Vitro Murine Lymphocyte Proliferation By Bacterial DNA." *The Journal of Immunology*, vol. 147(6):1759–1764.

Newman et al. (1991) "Survival of Human Macrophages Infected with *Mycobacterium avium* intracellulare Correlates with Increased Production of Tumor Necrosis Factor–α and IL–6." *The Journal of Immunology*, vol. 147(11):3942–3948.

Rao et al. (1993) "*Mycobacterium avium–M*. intracellulare Binds to the Integrin Receptor $α_vβ_3$ on Human Monocytes and Monocyte–Derived Macrophages." *Infection and Immunity*, vol. 61(2):663–670.

Roecklein et al. (1992) "Nonopsonic uptake of *Mycobacterium avium* complex by human monocytes and alveolar macrophages." *J. Lab. Clin. Med.*, vol. 119:772–781.

Roman et al. (1997) "Immunostimulatory DNA sequences functions T helper–1–promoting adjuvants." *Nature Medicine*, vol. 3(8):849–854.

Sparwasser et al. (1997) "Macrophages sense pathogens via DNA motifs: indujction of tumor necrosis factor–α–mediated shock." *Eur. J. Immunol.*, vol. 27:1671–1679.

Sparwasser et al. (1998) "Bacterial DNA and immunostimulatory CpG oligonucleotides trigger maturation and activation of murine dendritic cells." *Eur. J. Immunol.*, vol. 28:2045–2054.

Stacey et al. (1999) "Immunostimulatory DNA as an Adjuvant in Vaccination against Lieshmania major." *Infection and Immunity*, vol. 67(8):3719–3726.

Stacey et al. (1996) "Macrophages Ingest and Are Activated by Bacterial DNA." *J. Immunol.*, vol. 157:2116–2122.

Toulme (2001) "New candidates for true antisense." *Nature Biotechnology*, vol. 19:17–18.

Velaz–Faircloth et al. (1999) "Protect against *Mycobacterium avium* by DNA Vaccines Expressing Mycobacterial Antigens as Fusion Proteins with Green Fluorescent Protein." *Infection and Immunity*, vol. 4243–4250.

Walker et al. (1999) "Immunostimulatory oligodeoxynucleotides promote protective immunity and provide systemic therapy for leishmaniasis via IL–12– and IFN–γ–dependent mechanism." *Proc. Natl. Acad. Sci. USA*, vol 96:6970–6975.

Yamamoto et al. (1992) "DNA from Bacteria, but Not from Vertebrates, Induces Interferons, Activates Natural Killer Cells and Inhibits Tumor Growth." *Microbiol. Immunol.*, vol. 36(9):983–997.

Zimmermann et al. (1998) "Cutting Edge: CpG Oligodeoxynucleotides Trigger Protective and Curative Th1 Responses in Lethal Murine Leishmaniasis." *The Journal of Immunology*, vol. 160:3627–3630..

* cited by examiner

SEQUENCE LISTING

<160> NUMBER OF SEQ ID NOS: 7

<210> SEQ ID NO 1
<211> LENGTH: 22
<212> TYPE: DNA
<213> ORGANISM: Artificial Sequence
<220> FEATURE:
<223> OTHER INFORMATION: Immunomodulatory sequence

<400> SEQUENCE: 1
tgactgtgaa cgttcgagat ga                                        22

<210> SEQ ID NO 2
<211> LENGTH: 22
<212> TYPE: DNA
<213> ORGANISM: Artificial Sequence
<220> FEATURE:
<223> OTHER INFORMATION: Control sequence

<400> SEQUENCE: 2
tgactgtgaa ggttcgagat ga                                        22

<210> SEQ ID NO 3
<211> LENGTH: 22
<212> TYPE: DNA
<213> ORGANISM: Artificial Sequence
<220> FEATURE:
<223> OTHER INFORMATION: Control sequence

<400> SEQUENCE: 3
tgactgtgaa ggttagagat ga                                        22

<210> SEQ ID NO 4
<211> LENGTH: 24
<212> TYPE: DNA
<213> ORGANISM: Artificial Sequence
<220> FEATURE:
<223> OTHER INFORMATION: primer

<400> SEQUENCE: 4
ttatgcagac tgtgtcctgg caaa                                      24

<210> SEQ ID NO 5
<211> LENGTH: 24
<212> TYPE: DNA
<213> ORGANISM: Artificial Sequence
<220> FEATURE:
<223> OTHER INFORMATION: primer

<400> SEQUENCE: 5
tttccagcca gacagatata tgcg                                      24

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
accacagtcc atgccatcac                                           20

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
tccaccaccc tgttgctgta                                           20

IMMUNOMODULATORY POLYNUCLEOTIDES IN TREATMENT OF AN INFECTION BY AN INTRACELLULAR PATHOGEN

CROSS-REFERENCE To RELATED APPLICATIONS

This application is claims the benefit of U.S. provisional patent application no. 60/179,353, filed Jan. 31, 2000, which is incorporated herein by reference in its entirety.

STATEMENT AS TO FEDERALLY SPONSORED RESEARCH

This invention was made, at least in part, with a government grant from the National Institutes of Health (NIH Grant Nos. AI40682, AI47078, and HL57911). Thus, the U.S. government may have certain rights in this invention.

FIELD OF THE INVENTION

The invention relates generally to the field of prevention and treatment of infectious diseases, particularly infection by intracellular pathogens such as Mycobacterium.

BACKGROUND OF THE INVENTION

The broad classification of intracellular pathogens includes viruses, bacteria, protozoa, fungi, and intracellular parasites. These virulent pathogens multiply within the cells of the infected host organism rather than extracellularly and are major causes of morbidity and fatality world-wide. For example, intracellular pathogens are responsible for an estimated 10,000,000 new cases of tuberculosis per year in the world (approximately 25,000 per year in the United States), approximately 3,000,000 deaths per year from tuberculosis, an estimated 12,000,000 cases of leprosy, and an estimated 10,000,000 cases of American trypanosomiasis (Chagas disease). Furthermore, intracellular pathogens also cause other important diseases including cutaneous and visceral leishmaniasis, listeriosis, toxoplasmosis, histoplasmosis, trachoma, psittacosis, Q-fever, and Legionellosis including Legionnaires' disease. Few vaccines are available against such diseases and the pathogens are developing resistance to commonly used drugs.

One particular genus of intracellular bacteria, Mycobacteria, is a significant cause of morbidity and mortality, particularly among immunocompromised or elderly individuals and in countries with limited medical resources. Ninety-five percent of human infections are caused by seven species: *Mycobacterium tuberculosis, M. avium* (also known as the mycobacterium avium complex or *M. avium-intracellulare*), *M. leprae, M. kansasii, M. fortuitum, M. chelonae,* and *M. absecessus.* The most common mycobacterial infections in the United States are pulmonary infections by *M. tuberculosis* or *M. avium.* Such mycobacterial infections have been of increasing concern over the past decade, particularly in light of the increasing incidence of multi-drug resistant strains.

*M. tuberculosis* is the causative agent of tuberculosis, the classic human mycobacterial disease. Disease is spread by close person-to-person contact through inhalation of infectious aerosols; infection can be established if as few as one to three bacilli reach the alveolar spaces. Estimates indicates that one-third of the world's population, including 10 million in the U.S., are infected with *M. tuberculosis*, with 8 million new cases and 3 million deaths reported world wide each year. Although incidence of tuberculosis steadily decreased since the early 1900s, this trend changed in 1984 with increased immigration from endemic countries and increased infection in the homeless, drug and alcohol abusers, prisoners, and HIV-infected individuals ((1995) *Morbid. Mortal. Weekly Rep* 44:1–87). Due to the difficulties in eradicating disease in most of these populations, tuberculosis has again threatened to pose a significant public health risk.

*Mycobacterium avium* is generally less of a health risk for individuals with normal immune responses; *M. avium* can transiently colonize these individuals, but disease due to *M. avium* is rare. However, *M. avium* infection can cause serious disease in patients having compromised pulmonary function (e.g., patients with chronic bronchitis, obstructive pulmonary disease, or pre-existing pulmonary damage (e.g., due to previous pulmonary infections or other disease). Infection in individuals having compromised pulmonary function is clinically very similar to infection by *M. tuberculosis.*

*M. avium* infection poses the greatest health risk to immunocompromised individuals, and is one of the most common opportunistic infections in patients with AIDS (Horsburgh (1991) *New Eng. J. Med.* 324:1332–1338). In contrast with disease in other patients, *M. avium* infection can be very serious in immunocompromised individuals (e.g., AIDS patients, who have a low CD4+ T-cell count (Crowe, et al. (1991) *J. AIDS* 4:770–776)), and can result in disseminated infection in which virtually no organ is spared. The magnitude of such disseminated *M. avium* infections is overwhelming, with the bacterial load in some patients resulting in tissues that are literally filled with mycobacteria and with hundreds to thousands of bacilli per milliliter of blood. When disseminated disease occurs, *M. avium* infection results in considerable morbidity, and is a significant contributor to mortality in AIDS patients. Although highly active anti-retroviral therapy currently used to treat HIV-infected patients prevents the onset of *M. avium* infection to some extent (Autran, et al. (1997) *Science.* 277:112–116), this infection is extremely difficult to treat when encountered because of its poor responsiveness to anti-mycobacterial therapy (Chin, et al. (1994) *J. Infect. Dis.* 170:578–584; Masur (1993) *New Eng. J. Med.* 329:898–904).

As noted above, mycobacterial infection is normally acquired through inhalation of aerosolized infectious particles. Following inhalation, mycobacteria predominately infect and multiply within macrophages (Edwards, et al. (1986) *Am. Rev. Respir. Dis.* 134:1062–1071). The bacteria attach to and enter macrophages with the help of specific receptors expressed on the surface of these cells (Bermudez, et al. (1991) *Infect. Immun.* 59:1697–1702; Rao, et al. (1993) *Infect. Immun.* 61:663–670; Roecklein, et al. (1992) *J. Lab. Clin. Med.* 119:772–781). Studies have shown that macrophages secrete several cytokines such as tumor necrosis factor (TNF)-β, interleukin (IL)-1β, IL-6, granulocyte macrophage colony stimulating factor (GM-CSF), and granulocyte colony stimulating factor (Fattorini, et al. (1994) *J. Med. Microbiol.* 40:129–133; Newman, et al. (1991) *J. Immunol.* 147:3942–3948) in response to infection with mycobacteria. T cell products such as interferon (IFN)-γ and IL-12 are known to be extremely important for anti-mycobacterial activity of macrophages (Fattorini, et al. (1994) *J. Med. Microbiol.* 40:129–133) as well as in vivo in humans and mice (Appelberg, et al. (1994) *Infect. Immun.* 62:3962–3971; Holland, et al. (1994) *New Eng. J. Med.* 330:1348–1355; Kobayashi, et al. (1995) *Antimicrob. Agents Chemotherapy.* 39:1369–1371).

Treatment of mycobacterial infections is complicated and difficult. For example, treatment of *M. tuberculosis* and of M. avium infections requires a combination of relatively toxic agents, usually three different drugs, for at least six months. The toxicity and intolerability of these medications usually result in low compliance and inadequate treatment, which in turn increases the chance of therapeutic failure and enhances the selection for drug-resistant organisms. Treatment of mycobacterial infections is further complicated in pregnant women, patients with pre-existing liver or renal diseases, and immunocompromised patients, e.g., AIDS patients.

Immunomodulatory sequences (hereinafter referred to as "ISS") were initially discovered in the mycobacterial genome as DNA sequences that selectively enhance NK cell activity (Yamamoto, et al. (1992) *Microbiol. Immunol.* 36:983–997). Uptake of mycobacterial DNA or ISS has been shown to activate cells of the innate immune system, such as NK cells and macrophages and stimulating a type-1 like response (Roman, et al. (1997) *Nature Med.* 3:849–854). Further, administration of ISS has been shown activate NK cells (Krieg, A et al. (1995) *Nature.* 374:546–549), stimulate B cells to proliferate and to produce IgM antibodies (Krieg, A et al. (1995) *Nature.* 374:546–549; Messina, et al. (1991) *J. Immunol.* 147:1759–1764; ), stimulate production of cytokines, such as IFNs, IL-12, IL-18 and TNF-α (Sparwasser, et al. (1998) *Eur. J. Immunol.* 28:2045–2054; Sparwasser, et al. (1997) *Eur. J. Immunol.* 27:1671–1679; Stacey, et al. (1999) *Infect. Immun.* 67:3719–3726; Stacey, et al. (1996) *J. Immunol.* 157:2116–2122; Halpern, et al (1996) *Cell. Immunol.* 167:72–78; Klinman, et al. (1996) *Proc. Natl. Acad. Sci. U.S.A.* 93:2879–2883) and up-regulate co-stimulatory receptors (Martin-Orozco, et al. (1999) *Int. Immun.* 11:1111–1118; Sparwasser, et al. (1998) *Eur. J. Immunol.* 28:2045–2054).

Previous studies have demonstrated the ability of immunomodulatory nucleic acid to enhance innate immunity and host survival against intracellular pathogens such as *Listeria monocytogenes*, *Leishmania major*, and *Francisella tularensis* (Krieg, et al. (1998) *J. Immunol.* 161:2428–2434; Walker, et al. (1999) *Proc. Natl. Acad. Sci. U.S.A.* 96:6970–6975; Zimmermann, et al. (1998) *J. Immunol.* 160:3627–3630; Klinman, et al. (1999) *Infect. Immun.* 67:5658–5663). Walker, et al. found that injection of BALB/c mice with CpG-ODN 1826 four hours after inoculation with live *L. major* promastigote organisms protected 65% of animals tested from progressive infection, suggesting that CpG-ODN can redirect the harmful immune response elicited by live *L. major* parasites and that CpG-ODN might be efficacious in the treatment of early leishmaniasis (Walker, et al. (1999) *Proc. Natl. Acad. Sci. U.S.A.* 96:6970–6975). Zimmnermann et al. report that single injections of CpG-ODN protected *L. major*-infected BALB/c mice when given during the first 8 days of infection but failed when given later. Zimmermann also found that 5 of 6 *L. major*-infected BALB/c mice were able to control the infection when given three consecutive doses of CpG-ODN at 5 day intervals starting on day 15 or 20 post infection (Zimmermann, et al. (1998) *J. Immunol.* 160:3627–3630).

In their studies with *L. monocytogenes*, Kreig, et al. found that IFN-γ production is induced rapidly by ISS administration, returning to the basal level within 24 hours, while IL-12 (p40 and p70) is induced immediately after infection and lasts for at least 8 days (Krieg, et al. (1998) *J. Immunol.* 161:2428–2434). In the murine leishmaniasis model, the serum IL-12 level in the ISS-treated mice was found to be 10-fold higher than *L. major*-infected control mice (Zimmermann, et al. (1998) *J. Immunol.* 160:3627–3360).

Exogenous administration of type-1 cytokines, such as IL-12 and IFN-γ increase protection against *M. avium* infection in humans and mice (Appelberg, et al. (1994) *Infect. Immun.* 62:3962–3971; Holland, et al. (1994) *New Eng. J. Med.* 330:1348–1355; Kobayashi, et al. (1995) *Antimicrob. Agents Chemotherapy.* 39:1369–1371). IFN-γ and IL-12 are known to be important in host anti-mycobacterial immunity (Doherty, et al. (1997) *J. Immunol.* 158:4822–4831; Doherty, et al. (1998) *J. Immunol.* 160:5428–5435). However, administration of such cytokines is potentially dangerous to the patient, is expensive and does not provide an attractive means of preventing or treating existing infections by intracellular pathogens. Furthermore, administration of these cytokines can itself be associated with undesirable side-effects which are due at least in part to toxicity, especially at dosages sufficient to stimulate the subject's immune system.

DNA vaccines may provide an alternative method for therapy. DNA vaccination with a plasmid which encodes *M. avium* antigens (65 kDa and antigen 85B) had a protective effect against *M. avium* infection in mice (Velaz-Faircloth, et al. (1999) *Infect. Immun.* 67:4243–4250). Similarly, plasmid DNA which encodes antigen 85B, ESAT-6 and MPT64 (Kamath, et al. (1999) *Infect. Immun.* 67:1702–1707), and hsp-65 (Bonato, et al. (1998) *Infect. Immun.* 66:169–175) yielded protective immunity against *M. tuberculosis* infection. Further DNA vaccines based upon administration of a polynucleotide encoding a mycobacterial antigen are described in WO 98/53075. However, while these methods appear promising, DNA vaccination requires identification of an antigen that will induce a protective immune response. Furthermore, the immune response elicited by these vaccines is predominantly a type-1 response (i.e., mediated by Th1 cells and primarily resulting in production of antibodies). As discussed above, a robust cellular immune type-1 immune response (i.e., an immune response mediated by Th1 cells and primarily resulting in activation of cytotoxic T cells, which secrete IFN-γ) is likely required to provide effective immunity against such intracellular pathogens. Finally, while DNA vaccines may provide some protection against infection in a preventive mode, their effectiveness against an ongoing infection is not proven.

There remains a need in the field for effective methods for the treatment and prevention of infection by intracellular pathogens.

SUMMARY OF THE INVENTION

The present invention features methods for treatment or prevention of infection by intracellular pathogen by administration of an immunomodulatory nucleic acid molecule (ISS). In one embodiment, ISS are administered in combination with another anti-pathogenic agent to provide a synergistic anti-pathogenic effect. In a preferred embodiment, the intracellular pathogen is Mycobacterium species.

A primary object of the invention is to provide an effective method for the prevention and/or treatment of intracellular pathogen infections in a host, particularly mycobacterial infections.

Another object of the invention is to enhance the anti-pathogenic activity, particularly the anti-mycobacterial activity, of conventional chemotherapeutics to facilitate more effective clearance of the organism from an active infection in a subject.

One advantage of the invention is that, since immunomodulatory nucleic acid molecules act through induction of the immune response of the host, the use of immunomodulatory nucleic acid molecules will not substantially result in the selection of resistant organisms. Still another advantage is that immunomodulatory nucleic acids acts in synergy with conventional antibiotics, particularly in the context of treatment of mycobacterial infection.

These and other objects and advantages will be readily apparent to the ordinarily skilled artisan upon reading the disclosure provided herein.

BRIEF DESCRIPTION OF THE DRAWINGS

FIG. 11A represents results of semi-quantitative RT-PCR assessment of IDO induction in mice 16 hours after ISS injection. −, injected with saline; +, injected with ISS-ODN. FIG. 11B represents results of semi-quantitative RT-PCR assessment of IDO induction in ISS-ODN pre-treated mBMDM 4, 8, and 24 hours after infection with M. avium. 1, medium alone; 2, ISS-ODN treatment alone; 3, M. avium infection alone; 4, ISS-ODN treatment and M. avium infection.

DETAILED DESCRIPTION OF THE INVENTION

Figure 1:
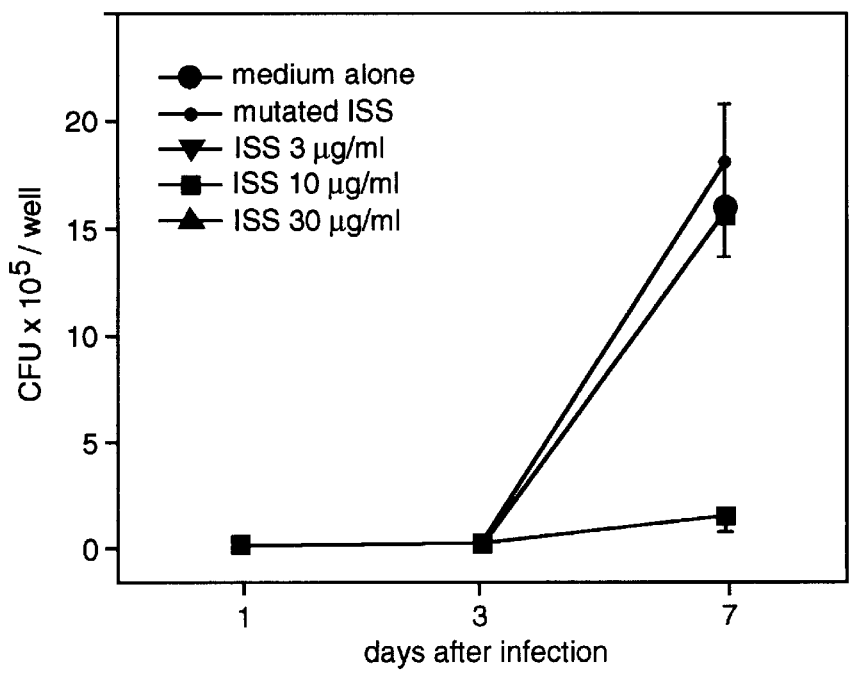
FIG. 1 is a graph showing the effect of immunomodulatory nucleic acid molecules (ISS), exemplified here by immunomodulatory DNA oligonucleotides (ISS-ODN), on intracellular growth of M. avium in human monocyte-derived macrophages (hMDM) in vitro. Results shown are representative of three experiments. Closed circles, medium alone; small diamonds, mutated ISS; inverted triangle, ISS at 3 µg/ml; closed square, ISS at 10 µg/ml; and closed triangle, ISS at 30 µg/ml.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a cell" includes a plurality of such cells and reference to "the polynucleotide" includes reference to one or more polynucleotides and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

As used herein, the term "pathogen" or "intracellular pathogen" or "microbe" refers to any organism that exists within a host cell, either in the cytoplasm or within a vacuole, for at least part of its reproductive or life cycle. Intracellular pathogens include viruses (e.g., CMV HIV), bacteria (e.g., Listeria, Mycobacteria, Salmonella (e.g., *S. typhi*) enteropathogenic *Escherichia coli* (EPEC), enterohaemorrhagic *Escherichia coli* (EHEC), Yersinia, Shigella, Chlamydia, Chlamydophila, Staphylococcus, Legionella), protozoa (e.g., Taxoplasma), fungi, and intracellular parasites (e.g., Plasmodium (e.g., *P. vivax, P. falciparum, P. ovale*, and *P. malariae*).

The terms "irnrunomodulatory nucleic acid molecule," "ISS," "ISS-PN," and "ISS-ODN," used interchangeably herein, refer to a polynucleotide that comprises at least one immunomodulatory nucleic acid moiety. The term "immunomodulatory," as used herein in reference to a nucleic acid molecule, refers to the ability of a nucleic acid molecule to modulate an immune response in a vertebrate host.

The terms "oligonucleotide," "polynucleotide," and "nucleic acid molecule", used interchangeably herein, refer to polymeric forms of nucleotides of any length, either ribonucleotides or deoxyribonucleotides. Thus, this term includes, but is not limited to, single-, double-, or multistranded DNA or RNA, genomic DNA, cDNA, DNA-RNA hybrids, or a polymer comprising purine and pyrimidine bases or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidites, and/or phosphorothioates, and thus can be an oligodeoxynucleoside phosphoramidate or a mixed phosphoramidate-phosphodiester oligomer. Peyrottes et al. (1996) *Nucl. Acids Res.* 24:1841–1848; Chaturvedi et al. (1996) *Nucl. Acids Res.* 24:2318–2323. The polynucleotide may comprise one or more L-nucleosides. A polynucleotide may comprise modified nucleotides, such as methylated nucleotides and nucleotide analogs, uracyl, other sugars, and linking groups such as fluororibose and thioate, and nucleotide branches. The sequence of nucleotides may be interrupted by non-nucleotide components. A polynucleotide may be modified to comprise N3'-P5' (NP) phosphoramidate, morpholino phosphorociamidate (MF), lockaed nucleic acid (LNA), 2'-O-methoxyethyl (MOE), or 2'-fluoro, arabino-nucleic acid (FANA), which can enhance the reistance of the polynucleotide to nuclease degradation (see, e.g., Faria et al. (2001) *Nature Biotechnol.* 19:40–44; Toulme (2001) *Nature Biotechnol.* 19:17–18). A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support. Immunomodulatory nucleic acid molecules can be provided in various formulations, e.g., in association with liposomes, microencapsulated, etc., as described in more detail herein.

The terms "polypeptide," "peptide," and "protein", used interchangeably herein, refer to a polymeric form of amino acids of any length, which can include coded and non-coded amino acids, chemically or biochemically modified or derivatized amino acids, and polypeptides having modified peptide backbones. The term includes polypeptide chains modified or derivatized in any manner, including, but not limited to, glycosylation, formylation, cyclization, acetylation, phosphorylation, and the like. The term includes naturally-occurring peptides, synthetic peptides, and peptides comprising one or more amino acid analogs. The term includes fusion proteins, including, but not limited to, fusion proteins with a heterologous amino acid sequence, fusions with heterologous and homologous leader sequences, with or without N-terminal methionine residues; immunologically tagged proteins; and the like.

As used herein the term "isolated" is meant to describe a compound of interest that is in an environment different from that in which the compound naturally occurs. "Isolated" is meant to include compounds that are within samples that are substantially enriched for the compound of interest and/or in which the compound of interest is partially or substantially purified.

As used herein, the term "substantially purified" refers to a compound that is removed from its natural environment and is at least 60% free, preferably 75% free, and most preferably 90% free from other components with which it is naturally associated.

"Treatment" or "treating" as used herein means any therapeutic intervention in a subject, usually a mammalian subject, generally a human subject, including: (i) prevention, that is, causing the clinical symptoms not to develop, e.g., preventing infection and/or preventing progression to a harmful state; (ii) inhibition, that is, arresting the development or further development of clinical symptoms, e.g., mitigating or completely inhibiting an active (ongoing) infection so that pathogen load is decreased to the degree that it is no longer harmful, which decrease can include complete elimination of an infectious dose of the pathogen from the subject; and/or (iii) relief, that is, causing the regression of clinical symptoms, e.g., causing a relief of fever, inflammation, and/or other symptoms caused by an infection.

As used herein, "immunoprotective response" is meant to encompass humoral and/or cellular immune responses that are sufficient to: 1) inhibit or prevent infection by an intracellular pathogen, particularly Mycobacteria; and/or 2) prevent onset of disease, reduce the risk of onset of disease, or reduce the severity of disease symptoms caused by infection by an intracellular pathogen, particularly Mycobacteria.

The term "effective amount" or "therapeutically effective amount" means a dosage sufficient to provide for treatment for the disease state being treated or to otherwise provide the desired effect (e.g., induction of an effective immune response). The precise dosage will vary according to a variety of factors such as subject-dependent variables (e.g., age, immune system health, etc.), the disease (e.g., the species of the infecting pathogen), and the treatment being effected. In the case of an intracellular pathogen infection, an "effective amount" is that amount necessary to substantially improve the likelihood of treating the infection, in particular that amount which improves the likelihood of successfully preventing infection or eliminating infection when it has occurred.

By "subject" or "individual" or "patient" is meant any subject for whom or which therapy is desired. Human subjects are of particular interest. Other subjects may include non-human primates, cattle, sheep, goats, dogs, cats, birds (e.g., chickens or other poultry), guinea pigs, rabbits, rats, mice, horses, and so on. Of particular interest are subjects having or susceptible to intracellular pathogen infection, particularly mycobacterial infection, more particularly to infection by *M. tuberculosis, M. avium*, and the like.

Overview

The invention is based on the discovery that: 1) administration of immunomodulatory nucleic acid molecules results in induction of an immune response protective against infection by mycobacteria; 2) immunomodulatory nucleic acid molecules act as a chemotherapeutic agent (as evidenced by, for example, the ability of immunomodulatory nucleic acid molecules to inhibit growth of mycobacteria when administered alone); 3) immunomodulatory nucleic acid molecules provide a synergistic effect when administered with another chemotherapeutic agent; and 4) administration of immunomodulatory nucleic acid molecules results in induction of indoleamine 2,3-dioxygenase (IDO), indicating immunomodulatory nucleic acid molecules have activity against a wide range of intracellular pathogens that utilize L-tryptophan of the host cell. In short, immunomodulatory nucleic acid molecule administration results in activation of the subject's innate immunity and induction of IDO synthesis, takes advantage of chemotherapeutic activity of the immunomodulatory nucleic acid molecules, and can thus modify the course of infection by an intracellular pathogen.

Various aspects of the invention will now be described in more detail.

Nucleic Acid Molecules Comprising Immunomodulatory Nucleic Acid Molecule

Immunomodulatory nucleic acid molecules are polynucleotides that modulate activity of immune cells, especially immune cell activity associated with a type-1 (Th1-mediated) or type-1 like immune response. Furthermore, immunomodulatory nucleic acid molecules of the present invention encompass polynucleotides that inhibit replication of intracellular pathogens (e.g., inhibit intracellular mycobacterial replication.).

Nucleic acid molecules comprising an immunomodulatory nucleic acid molecule which are suitable for use in the methods of the invention include an oligonucleotide, which can be a part of a larger nucleotide construct such as a plasmid. The term "polynucleotide" therefore includes oligonucleotides, modified oligonucleotides and oligonucleosides, alone or as part of a larger construct. The polynucleotide can be single-stranded DNA (ssDNA), double-stranded DNA (dsDNA), single-stranded RNA (ssRNA) or double-stranded RNA (dsRNA). The polynucleotide portion can be linearly or circularly configured, or the oligonucleotide portion can contain both linear and circular segments. Immunomodulatory nucleic acid molecules also encompasses crude, detoxified bacterial (e.g., mycobacterial) RNA or DNA, as well as ISS-enriched plasmids. "ISS-enriched plasmid" as used herein is meant to refer to a linear or circular plasmid that comprises or is engineered to comprise a greater number of CpG motifs than normally found in mammalian DNA. Exemplary ISS-enriched plasmids are described in, for example, Roman et al. (1997) *Nat Med.* 3(8):849–54. Modifications of oligonucleotides include, but are not limited to, modifications of the 3'OH or 5'OH group, modifications of the nucleotide base, modifications of the sugar component, and modifications of the phosphate group.

The immunomodulatory nucleic acid molecule can comprise ribonucleotides (containing ribose as the only or principal sugar component), deoxyribonucleotides (containing deoxyribose as the principal sugar component), or in accordance with the established state-of-the-art, modified sugars or sugar analogs may be incorporated in the oligonucleotide of the present invention. Examples of a sugar moiety that can be used include, in addition to ribose and deoxyribose, pentose, deoxypentose, hexose, deoxyhexose, glucose, arabinose, xylose, lyxose, and a sugar "analog" cyclopentyl group. The sugar may be in pyranosyl or in a furanosyl form. In the modified oligonucleotides of the present invention, the sugar moiety is preferably the furanoside of ribose, deoxyribose, arabinose or 2'-O-methylribose, and the sugar may be attached to the respective heterocyclic bases either in I or J anomeric configuration.

An immunomodulatory nucleic acid molecule may comprise at least one nucleoside comprising an L-sugar. The L-sugar may be deoxyribose, ribose, pentose, deoxypentose, hexose, deoxyhexose, glucose, galactose, arabinose, xylose, lyxose, or a sugar "analog" cyclopentyl group. The L-sugar may be in pyranosyl or furanosyl form.

The phosphorous derivative (or modified phosphate group) that can be attached to the sugar or sugar analog moiety in the modified oligonucleotides of the present invention can be a monophosphate, diphosphate, triphosphate, alkylphosphate, alkanephosphate, phosphoronthioate, phosphorodithioate or the like. The heterocyclic bases, or nucleic acid bases that are incorporated in the oligonucleotide base of the ISS can be the naturally occurring principal purine and pyrimidine bases, (namely uracil or thymine, cytosine, adenine and guanine, as mentioned above), as well as naturally occurring and synthetic modifications of said principal bases. Those skilled in the art will recognize that a large number of "synthetic" non-natural nucleosides comprising various heterocyclic bases and various sugar moieties (and sugar analogs) are available, and that the immunomodulatory nucleic acid molecule can include one or several heterocyclic bases other than the principal five base components of naturally occurring nucleic acids. Preferably, however, the heterocyclic base in the ISS is selected from uracil-5-yl, cytosin-5-yl, adenin-7-yl, adenin-8-yl, guanin-7-yl, guanin-8-yl, 4-aminopyrrolo [2,3-d] pyrimidin-5-yl, 2-amino-4-oxopyrolo [2,3-d] pyrimidin-5-yl, 2-amino-4-oxopyrrolo [2,3-d] pyrimidin-3-yl groups, where the purines are attached to the sugar moiety of the oligonucleotides via the 9-position, the pyrimidines via the 1-position, the pyrrolopyrimidines via the 7-position and the pyrazolopyrimidines via the 1-position.

Structurally, the root oligonucleotide of the immunomodulatory nucleic acid molecule is a non-coding sequence that can include at least one unmethylated CpG motif. The relative position of any CpG sequence in ISS with immunomodulatory activity in certain mammalian species (e.g., rodents) is 5'-CG-3' (i.e., the C is in the 5' position with respect to the G in the 3' position).

Immunomodulatory nucleic acid molecules generally do not provide for, nor is there any requirement that they provide for, expression of any amino acid sequence encoded by the polynucleotide, and thus the sequence of a immunomodulatory nucleic acid molecule may be, and generally is, non-coding. Immunomodulatory nucleic acid molecules may comprise a linear double or single-stranded molecule, a circular molecule, or can comprise both linear and circular segments. Immunomodulatory nucleic acid molecules may be single-stranded, or may be completely or partially double-stranded.

In some embodiments, an immunomodulatory nucleic acid molecule is an oligonucleotide, e.g., consists of a sequence of from about 6 to about 200, from about 10 to about 100, from about 12 to about 50, or from about 15 to about 25, nucleotides in length.

Exemplary consensus CpG motifs of immunomodulatory nucleic acid molecules useful in the invention include, but are not necessarily limited to:

5'-Purine-Purine-[C]-[G]-Pyrimidine-Pyrimidine-3', in which the immunomodulatory nucleic acid molecule comprises a CpG motif flanked by at least two purine nucleotides (e.g., GG, GA, AG, AA, II, etc.,) and at least two pyrimidine nucleotides (CC, TT, CT, TC, UU, etc.);

5'-Purine-TCG-Pyrimidine-Pyrimidine-3';

5'-[TCG]$_n$-3', where n is any integer that is 1 or greater, e.g., to provide a poly-TCG immunomodulatory nucleic acid molecule (e.g., where n=3, the polynucleotide comprises the sequence 5'-TCGTCGTCG-3'); and 5'-Purine-Purine-CG-Pyrimidine-Pyrimidine-CG-3'.

5'-Purine-TCG-Pyrimidine-Pyrimidine-CG-3'

Exemplary DNA-based immunomodulatory nucleic acid molecules useful in the invention include, but are not necessarily limited to, polynucleotides comprising the following nucleotide sequences:

```
AACGCC, AACGCT, AACGTC, AACGTT;

AGCGCC, AGCGCT, AGCGTC, AGCGTT;

GACGCC, GACGCT, GACGTC, GACGTT;

GGCGCC, GGCGCT, GGCGTC, GGCGTT;

ATCGCC, ATCGCT, ATCGTC, ATCGTT;

GTCGCC, GTCGCT, GTCGTC, GTCGTT; and

TCGTCG, and TCGTCGTCG.
```

Octameric sequences are generally the above-mentioned hexameric sequences, with an additional 3' CG. Exemplary DNA-based immunomodulatory nucleic acid molecules useful in the invention include, but are not necessarily limited to, polynucleotides comprising the following octameric nucleotide sequences:

```
AACGCCCG, AACGCTCG, AACGTCCG, AACGTTCG;

AGCGCCCG, AGCGCTCG, AGCGTCCG, AGCGTTCG;

GACGCCCG, GACGCTCG, GACGTCCG, GACGTTCG;

GGCGCCCG, GGCGCTCG, GGCGTCCG, GGCGTTCG;

ATCGCCCG, ATCGCTCG, ATCGTCCG, ATCGTTCG;

GTCGCCCG, GTCGCTCG, GTCGTCCG, and GTCGTTCG.
```

Immunomodulatory nucleic acid molecules useful in the invention can comprise one or more of any of the above CpG motifs. For example, immunomodulatory nucleic acid molecules useful in the invention can comprise a single instance or multiple instances (e.g., 2, 3, 5 or more) of the same CpG motif. Alternatively, the immunomodulatory nucleic acid molecules can comprises multiple CpG motifs (e.g., 2, 3, 5 or more) where at least two of the multiple CpG motifs have different consensus sequences, or where all CpG motifs in the immunomodulatory nucleic acid molecules have different consensus sequences.

A non-limiting example of an immunomodulatory nucleic acid molecule is one with the sequence 5'-TGACTGTGAACGTTCGAGATGA-3' (SEQ ID NO:1). An example of a control nucleic acid molecule is one having the sequence 5'-TGACTGTGAAgGTTCGAGATGA-3' (SEQ ID NO:2), which differs from SEQ ID NO:1 at the nucleotide indicated in lower case type.

Immunomodulatory nucleic acid molecules useful in the invention may or may not include palindromic regions. If present, a palindrome may extend only to a CpG motif, if present, in the core hexamer or octamer sequence, or may encompass more of the hexamer or octamer sequence as well as flanking nucleotide sequences.

The core hexamer structure of the foregoing immunomodulatory nucleic acid molecules can be flanked upstream and/or downstream by any number or composition of nucleotides or nucleosides. However, ISS are at least 6 bases in length, and preferably are between 6 and 200 bases in length, to enhance uptake of the immunomodulatory nucleic acid molecule into target tissues.

In particular, immunomodulatory nucleic acid molecules useful in the invention include those that have hexameric nucleotide sequences having "CpG" motifs. Although DNA sequences are generally preferred, RNA immunomodulatory nucleic acid molecules can be used, with inosine and/or uracil substitutions for nucleotides in the hexamer sequences.

Modifications

Immunomodulatory nucleic acid molecules can be modified in a variety of ways. For example, the immunomodulatory nucleic acid molecules can comprise backbone phosphate group modifications (e.g., methylphosphonate, phosphorothioate, phosphoroamidate and phosphorodithioate internucleotide linkages), which modifications can, for example, enhance stability of the immunomodulatory nucleic acid molecule in vivo, making them particularly useful in therapeutic applications. A particularly useful phosphate group modification is the conversion to the phosphorothioate or phosphorodithioate forms of an immunomodulatory nucleic acid molecule. Phosphorothioates and phosphorodithioates are more resistant to degradation in vivo than their unmodified oligonucleotide counterparts, increasing the half-lives of the immunomodulatory nucleic acid molecules and making them more available to the subject being treated.

Other modified immunomodulatory nucleic acid molecules encompassed by the present invention include immunomodulatory nucleic acid molecules having modifications at the 5' end, the 3' end, or both the 5' and 3' ends. For example, the 5' and/or 3 end can be covalently or non-covalently conjugated to a molecule (either nucleic acid, non-nucleic acid, or both) to, for example, increase the bio-availability of the immunomodulatory nucleic acid molecules, increase the efficiency of uptake where desirable, facilitate delivery to cells of interest, and the like. Exemplary molecules for conjugation to the immunomodulatory nucleic acid molecules include, but are not necessarily limited to, cholesterol, phospholipids, fatty acids, sterols, oligosaccharides, polypeptides (e.g., immunoglobulins), peptides, antigens (e.g., peptides, small molecules, etc.), linear or circular nucleic acid molecules (e.g., a plasmid), and the like. Additional immunomodulatory nucleic acid conjugates, and methods for making same, are known in the art and described in, for example, WO 98/16427 and WO 98/55495. Thus, the term "immunomodulatory nucleic acid molecule" includes conjugates comprising an immunomodulatory nucleic acid molecule.

Preparation of Immunomodulatory Nucleic Acid Molecules

Immunomodulatory nucleic acid molecules can be synthesized using techniques and nucleic acid synthesis equipment well known in the art (see, e.g., Ausubel et al. Current Protocols in Molecular Biology, (Wiley Intersicence, 1989); Maniatis et al. Molecular Cloning: A Laboratory Manual (Cold Spring Harbor Laboratories, New York, 1982); and U.S. Pat. Nos. 4,458,066; and 4,650,675. Individual polynucleotide fragments can be ligated with a ligase such as T4 DNA or RNA ligase as described in, e.g., U.S. Pat. No. 5,124,246. Oligonucleotide degradation can be accomplished through exposure to a nuclease, see, e.g., U.S. Pat. No. 4,650,675. As noted above, since the immunomodulatory nucleic acid molecules need not provide for expression of any encoded amino acid sequence, the invention does not require that the immunomodulatory nucleic acid molecules be operably linked to a promoter or otherwise provide for expression of a coding sequence.

Alternatively, immunomodulatory nucleic acid molecules can be isolated from microbial species (e.g., mycobacteria) using techniques well known in the art such as nucleic acid hybridization, amplification (e.g., by PCR), and the like. Isolated immunomodulatory nucleic acid molecules can be purified to a substantially pure state, e.g., free of endogenous contaminants, e.g., lipopolysaccharides. Immunomodulatory nucleic acid molecules isolated as part of a larger polynucleotide can be reduced to the desired length by techniques well known in the art, such as endonuclease digestion. Other techniques suitable for isolation, purification, and production of polynucleotides to obtain ISS will be readily apparent to the ordinarily skilled artisan in the relevant field.

Circular immunomodulatory nucleic acid molecules can also be synthesized through recombinant methods or chemically synthesized. Where circular immunomodulatory nucleic acid molecules are obtained through isolation or recombinant methods, the immunomodulatory nucleic acid molecule can be provided as a plasmid. Chemical synthesis of smaller circular oligonucleotides can be performed using methods known in the art (see, e.g., Gao et al. (1995) *Nucl. Acids. Res.* 23:2025–9; Wang et al., (1994) *Nucl. Acids Res.* 22:2326–33).

Where the immunomodulatory nucleic acid molecule comprises a modified oligonucleotide, the modified oligonucleotides can be synthesized using standard chemical techniques. For example, solid-support based construction of methylphosphonates has been described in Agrawal et al. *Tet. Lett.* 28:3539–42. Synthesis of other phosphorous-based modified oligonucleotides, such as phosphotriesters (see, e.g., Miller et al. (1971) *J. Am Chem Soc.* 93:6657–65), phosphoramidates (e.g., Jager et al. (1988) *Biochem.* 27:7237–46), and phosphorodithioates (e.g., U.S. Pat. No. 5,453,496) is known in the art. Other non-phosphorous-based modified oligonucleotides can also be used (e.g., Stirchak et al. (1989) *Nucl. Acids. Res.* 17:6129–41).

Preparation of base-modified nucleosides, and the synthesis of modified oligonucleotides using such base-modified nucleosides as precursors is well known in the art, see, e.g., U.S. Pat. Nos. 4,910,300; 4,948,882; and 5,093,232. These base-modified nucleosides have been designed so that they can be incorporated by chemical synthesis into either terminal or internal positions of an oligonucleotide. Nucleosides modified in their sugar moiety have also been described (see, e.g., U.S. Pat. Nos. 4,849,513; 5,015,733; 5,118,800; and 5,118,802).

Techniques for making phosphate group modifications to oligonucleotides are known in the art. Briefly, an intermediate phosphate triester for the target oligonucleotide product is prepared and oxidized to the naturally-occurring phosphate triester with aqueous iodine or other agents, such as anhydrous amines. The resulting oligonucleotide phosphoramidates can be treated with sulfur to yield phosphorothioates. The same general technique (without the sulfur treatment step) can be used to produced methylphosphoamidites from methylphosphonates. Techniques for phosphate group modification are well known and are described in, for example, U.S. Pat. Nos. 4,425,732; 4,458,066; 5,218,103; and 5,453,496.

Identification of Immunomodulatory Nucleic Acid Molecules

Confirmation that a particular compound has the properties of an immunomodulatory nucleic acid molecule useful in the invention can be obtained by evaluating whether the immunomodulatory nucleic acid molecule elicits the appropriate cytokine secretion patterns, e.g., a cytokine secretion pattern associated with a type-1 immune response; inhibits intracellular pathogen replication, e.g., inhibits intracellular growth of intracellular pathogens either in vitro or in vivo; and/or modulates intracellular availability of cellular products necessary for growth and/or reproduction of the intracellular pathogen, e.g., reduces intracellular levels of L-tryptophan, for example, by inducing expression of indoleamine 2,3-dioxygenase (IDO) in a cell. ISS delivered with an antigen also induces activity of cytotoxic T cells and acts as a very strong mucosal adjuvant (see, e.g., Horner (1998) *Cell. Immunol.* 190:77–82). As noted above, immunomodulatory nucleic acid molecules of interest in the methods of the invention are those that elicit a Th1-mediated response, those that induce expression of IDO, and those that inhibit intracellular growth of intracellular pathogens, particularly intracellular growth of mycobacteria, more particularly intracellular mycobacterial growth in macrophages, especially monocyte-derived macrophages and bone marrow-derived macrophages.

In general, helper T (Th) cells are divided into broad groups based on their specific profiles of cytokine production: Th1, Th2, and Th0. "Th1" cells are T lymphocytes that release predominantly the cytokines IL-2 and IFN-γ, which cytokines in turn promote T cell proliferation, facilitate macrophage activation, and enhance the cytolytic activity of natural killer (NK) cells and antigen-specific cytotoxic T cells (CTL). In contrast, the cytokines predominantly released by Th2 cells are IL-4, IL-5, and IL-10. IL-4 and IL-5 are known to mediate antibody isotype switching towards IgE or IgA response, and promote eosinophil recruitment, skewing the immune system toward an "allergic" type of response. Th0 cells release a set of cytokines with characteristics of both Th1-type and Th2-type responses. While the categorization of T cells as Th1, TH2, or Th0 is helpful in describing the differences in immune response, it should be understood that it is more accurate to view the T cells and the responses they mediate as forming a continuum, with Th1 and Th2 cells at opposite ends of the scale, and Th0 cells providing the middle of the spectrum. Therefore, it should be understood that the use of these terms herein is only to describe the predominant nature of the immune response elicited, and is not meant to be limiting to an immune response that is only of the type indicated. Thus, for example, reference to a "type-1" or "Th1" immune response is not meant to exclude the presence of a "type-2" or "Th2" immune response, and vice versa.

Details of in vitro and in vivo techniques useful for evaluation of production of cytokines associated with a type-1 or type-2 response, as well as for evaluation of antibody production, are well known in the art. Likewise, methods for evaluating the ability of candidate ISS to inhibit intracellular pathogen growth are also well known in the art, and are further exemplified in the Examples below.

Administration of Immunomodulatory Nucleic Acid Molecules

Immunomodulatory nucleic acid molecules are administered to an individual using any available method and route suitable for drug delivery, including in vivo and ex vivo methods, as well as systemic, mucosal, and localized routes of administration.

Conventional and pharmaceutically acceptable routes of administration include intranasal, intramuscular, intratracheal, subcutaneous, intradermal, topical application, intravenous, rectal, nasal, oral and other parenteral routes of administration. Routes of administration may be combined, if desired, or adjusted depending upon the immunomodulatory nucleic acid molecule and/or the desired effect on the immune response. The immunomodulatory nucleic acid composition can be administered in a single dose or in multiple doses, and may encompass administration of booster doses, to elicit and/or maintain the desired effect on the immune response.

Immunomodulatory nucleic acid molecules can be administered to a subject using any available conventional methods and routes suitable for delivery of conventional drugs, including systemic or localized routes. Methods and localized routes that further facilitate production of a type-1 or type-1-like response and/or the anti-pathogenic (e.g. anti-mycobacterial) activity of the immunomodulatory nucleic acid molecules, particularly at or near a site of intracellular pathogen infection (e.g., within the lungs) is of interest in the invention, and may be preferred over systemic routes of administration, both for the immediacy of therapeutic effect and avoidance of in vivo degradation of the administered immunomodulatory nucleic acid molecules. In general, routes of administration contemplated by the invention include, but are not necessarily limited to, enteral, parenteral, or inhalational routes. Inhalational routes may be preferred in cases of pulmonary involvement, particularly in view of the activity of immunomodulatory nucleic acid molecules as a mucosal adjuvant.

Inhalational routes of administration (e.g., intranasal, intrapulmonary, and the like) are particularly useful in stimulating an immune response for prevention or treatment of intracellular pathogen infections of the respiratory tract. Such means include inhalation of aerosol suspensions or insufflation of the polynucleotide compositions of the invention. Nebulizer devices, metered dose inhalers, and the like suitable for delivery of polynucleotide compositions to the nasal mucosa, trachea and bronchioli are well-known in the art and will therefore not be described in detail here. For general review in regard to intranasal drug delivery, see, e.g., Chien, *Novel Drug Delivery Systems*, Ch. 5 (Marcel Dekker, 1992).

Parenteral routes of administration other than inhalation administration include, but are not necessarily limited to, topical, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery of immunomodulatory nucleic acid molecules. Where systemic delivery is desired, administration typically involves invasive or systemically absorbed topical or mucosal administration of pharmaceutical preparations.

Immunomodulatory nucleic acid molecules can also be delivered to the subject by enteral administration. Enteral routes of administration include, but are not necessarily limited to, oral and rectal (e.g., using a suppository) delivery.

Methods of administration of immunomodulatory nucleic acid molecules through the skin or mucosa include, but are not necessarily limited to, topical application of a suitable pharmaceutical preparation, transdermal transmission, injection and epidermal administration. For transdermal transmission, absorption promoters or iontophoresis are suitable methods. For review regarding such methods, those of ordinary skill in the art may wish to consult Chien, supra at Ch. 7. Iontophoretic transmission may be accomplished using commercially available "patches" which deliver their product continuously via electric pulses through unbroken skin for periods of several days or more. An exemplary patch product for use in this method is the LECTRO PATCH™ (manufactured by General Medical Company, Los Angeles, Calif.) which electronically maintains reservoir electrodes at neutral pH and can be adapted to provide dosages of differing concentrations, to dose continuously and/or to dose periodically.

Epidermal administration can be accomplished by mechanically or chemically irritating the outermost layer of the epidermis sufficiently to provoke an immune response to the irritant. An exemplary device for use in epidermal administration employs a multiplicity of very narrow diameter, short tynes which can be used to scratch ISS coated onto the tynes into the skin. The device included in the MONO-VACC™ tuberculin test (manufactured by Pasteur Merieux, Lyon, France) is suitable for use in epidermal administration of immunomodulatory nucleic acid molecules.

The invention also contemplates opthalmic administration of immunomodulatory nucleic acid molecules, which generally involves invasive or topical application of a pharmaceutical preparation to the eye. Eye drops, topical cremes and injectable liquids are all examples of suitable formulations for delivering drugs to the eye.

Immunomodulatory nucleic acid molecules can be administered to a subject prior to exposure to intracellular pathogen, after exposure to intracellular pathogen but prior to onset of disease symptoms associated with infection, or after intracellular pathogen infection or onset of disease symptoms. As such, immunomodulatory nucleic acids can be administered at any time after exposure to intracellular pathogen, but a first dose is usually administered about 8 hours, about 12 hours, about 24 hours, about 2 days, about 4 days, about 8 days, about 16 days, about 30 days or 1 month, about 2 months, about 4 months, about 8 months, or about 1 year after exposure to intracellular pathogen. As described in more detail below, the invention also provides for administration of subsequent doses of immunomodulatory nucleic acid molecules.

Administration with Additional Chemotherapeutic Agents

In one embodiment, immunomodulatory nucleic acid molecules are administered in combination with a conventional anti-pathogenic agent to provide for a synergistic effect in treatment of intracellular pathogen infection. The additional anti-pathogenic agent may be any agent (e.g., chemotherapeutic agent) identified as having activity against the intracellular pathogen of interest (e.g., in inhibition of extracellular or intracellular growth stages of the intracellular pathogen (e.g., mycobacteria), enhancement of intracellular pathogen clearance (e.g., mycobacteria), etc.). Exemplary anti-pathogenic agents include, but are not necessarily limited to, antibiotics, including antimicrobial agents, (e.g., bacteriostatic and bactericidal agents (e.g., aminoglycosides, β-lactam antibiotics, cephalosporins, macrolides, penicillins, tetracyclines, quinolones, and the like), antivirals (e.g., amprenavirs, acyclovirs, amantadines, virus penciclovirs, and the like), and the like), antifungals, (e.g., imidazoles, triazoles, allylamines, polyenes, and the like), as well as anti-parasitic agents (e.g., atovaquones, chloroquines, pyrimethamines, ivermectins, mefloquines, pentamidines, primaquines, and the like). Where the subject being treated is particularly susceptible to infection by intracellular pathogens, including opportunistic pathogens, it may be desirable to administer immunomodulatory nucleic acid molecules in a combination therapeutic regimen with chemotherapeutic agents that exhibit activity against microbial and/or parasitic pathogens, e.g., antimicrobial agents, antiviral agents, antifungal agents, anti-parasitic agents, etc. Such combination therapies can involve simultaneous or consecutive administration of ISS and such a chemotherapeutic agent(s).

Specific exemplary conventional anti-pathogenic/chemotherapeutic agents and combinatory therapies, particularly anti-mycobacterial agents and combinatory therapies, include, but are not necessarily limited to, clarithromycin (e.g., by oral administration or injection); capreomycin sulfate (e.g., by intramuscular injection or intravenous infusion, e.g., CAPASTAT®); ethambutol HCl (e.g., by oral administration of tablets or capsules, e.g., MYAMBUTOL®); isoniazid (e.g., by intramuscular injection or oral administration, e.g., NYDRAZID®); aminosalicylic acid (e.g., aminosalicyclic acid granules for oral administration, e.g., PASER® GRANULES); rifapentine (e.g., by oral administration; e.g., PRIFTIN®); PYRAZINAMIDE (e.g., by oral administration); rifampin (e.g., by oral administration, e.g., RIFADIN®, or by intravenous administration, e.g., RIFADIN IV®); rifampin and isoniazid combination therapy (e.g., by oral administration, e.g., RIFAMATE®); rifampin, isoniazid, and pyrazinamide combination therapy (e.g., by oral administration, e.g., RIFATER®); cycloserine (e.g., by oral administration, e.g., SEROMYCIN®); streptomycin sulfate (e.g., by injection or oral administration); ethionamide (e.g., by oral administration, e.g., TRECATOR®-SC), and the like.

The anti-pathogenic/chemotherapeutic agent and immunomodulatory nucleic acid molecule can be administered within the same or different formulation; by the same or different routes; or concurrently, simultaneously, or consecutively. The immunomodulatory nucleic acid molecule can be delivered according to a regimen (e.g., frequency during a selected interval (e.g., number of times per day), delivery route, etc.) that is the same as, similar to, or different from that of the anti-pathogenic agent. When administered in combination, ISS and an anti-pathogenic agent are generally administered within about 96 hours, about 72 hours, about 48 hours, about 24 hours, about 12 hours, about 8 hours, about 4 hours, about 2 hours, about 1 hour, or about 30 minutes or less, of each other. Thus, although it may be desirable to do so in some situations, it is not necessarily required that ISS and an anti-pathogenic agent (e.g., antibacterial agent) be delivered simultaneously.

Dosages

One particular advantage of the use of immunomodulatory nucleic acid molecules in the methods of the invention is that immunomodulatory nucleic acid molecules exert immunomodulatory and anti-pathogenic activity even at relatively low dosages. Although the dosage used will vary depending on the clinical goals to be achieved, a suitable dosage range is one which provides up to about 1 $\mu$g, to about 1,000 $\mu$g, to about 10,000 $\mu$g, to about 25,000 $\mu$g or about 50,000 $\mu$g of ISS. Immunomodulatory nucleic acid molecules can be administered in a single dosage or several smaller dosages over time. Alternatively, a target dosage of ISS can be considered to be about 1–10 $\mu$M in a sample of host blood drawn within the first 24–48 hours after administration of ISS. Based on current studies, immunomodulatory nucleic acid molecules are believed to have little or no toxicity at these dosage levels.

It should be noted that the immunotherapeutic activity of immunomodulatory nucleic acid molecules in the invention is essentially dose-dependent. Therefore, to increase ISS potency by a magnitude of two, each single dose is doubled in concentration. Increased dosages may be needed to achieve the desired therapeutic goal. The invention thus contemplates administration of "booster" doses to provide and maintain an immune response effective to protect the subject from infection or to inhibit infection; to reduce the risk of the onset of disease or the severity of disease symptoms that may occur as a result of infection; to facilitate reduction of intracellular pathogen load; and/or to facilitate clearance of infecting intracellular pathogen from the subject (e.g., to facilitate clearance of organisms from the lungs). When multiple doses are administered, subsequent doses are administered within about 16 weeks, about 12 weeks, about 8 weeks, about 6 weeks, about 4 weeks, about 2 weeks, about 1 week, about 5 days, about 72 hours, about 48 hours, about 24 hours, about 12 hours, about 8 hours, about 4 hours, or about 2 hours or less of the previous dose. In one embodiment, ISS are administered at intervals ranging from at least every two weeks to every four weeks (e.g., monthly intervals) in order to maintain the maximal immune response against intracellular pathogen infection (e.g., mycobacterial infection).

In view of the teaching provided by this disclosure, those of ordinary skill in the clinical arts will be familiar with, or can readily ascertain, suitable parameters for administration of ISS according to the invention.

Formulations

In general, immunomodulatory nucleic acid molecules are prepared in a pharmaceutically acceptable composition for delivery to a host. Pharmaceutically acceptable carriers preferred for use with the ISS of the invention may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. A composition of ISS may also be lyophilized using means well known in the art, for subsequent reconstitution and use according to the invention. Also of interest are formulations for liposomal delivery, and formulations comprising microencapsulated immunomodulatory nucleic acid molecules.

In general, the pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions comprising the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents. Preservatives and other additives may also be present such as, for example, anti-pathogenic agents (e.g., antimicrobials, antibacterials, antivirals, antifungals, etc.), antioxidants, chelating agents, and inert gases and the like. In one embodiment, as discussed above, the immunomodulatory nucleic acid molecule formulation comprises an additional anti-pathogenic agent. Exemplary anti-pathogenic agents include, but are not necessarily limited to, antibiotics, including antimicrobial agents (e.g., bacteriostatic and bacteriocidal agents (e.g., aminoglycosides, β-lactam antibiotics, cephalosporins, macrolides, penicillins, tetracyclines, quinolones, and the like), antivirals (e.g., amprenavirs, acyclovirs, amantadines, virus penciclovirs, and the like), and the like), antifungals, (e.g., imidazoles, triazoles, allylamines, polyenes, and the like), as well as anti-parasitic agents (e.g., atovaquones, chloroquines, pyrimethamines, ivermectins, mefloquines, pentamidines, primaquines, and the like). In another embodiment, the anti-pathogenic agent is an anti-mycobacterial agent (e.g., clarithromycin; capreomycin sulfate; ethambutol HCl; isoniazid; aminosalicylic acid; rifapentine; PYRAZINAMIDE; rifampin; rifampin and isoniazid in combination; rifampin, isoniazid, and pyrazinamide in combination; cycloserine; streptomycin sulfate; ethionamide; and the like).

Immunomodulatory nucleic acid molecules can be administered in the absence of agents or compounds that might facilitate uptake by target cells (e.g., as a "naked" polynucleotide, e.g., a polynucleotide that is not encapsulated by a viral particle). Immunomodulatory nucleic acid molecules can also be administered with compounds that facilitate uptake of immunomodulatory nucleic acid molecules by target cells (e.g., by macrophages) or otherwise enhance transport of the immunomodulatory nucleic acid molecules to a treatment site for action. Absorption promoters, detergents and chemical irritants (e.g., keratinolytic agents) can enhance transmission of an immunomodulatory nucleic acid molecule composition into a target tissue (e.g., through the skin). For general principles regarding absorption promoters and detergents which have been used with success in mucosal delivery of organic and peptide-based drugs, see, e.g. Chien, *Novel Drug Delivery Systems*, Ch. 4 (Marcel Dekker, 1992). Examples of suitable nasal absorption promoters in particular are set forth at Chien, supra at Ch. 5, Tables 2 and 3; milder agents are preferred. Suitable agents for use in the method of this invention for mucosal/nasal delivery are also described in Chang, et al., *Nasal Drug Delivery*, "Treatise on Controlled Drug Delivery", Ch. 9 and Tables 3–4B thereof, (Marcel Dekker, 1992). Suitable agents which are known to enhance absorption of drugs through skin are described in Sloan, Use of Solubility Parameters from Regular Solution Theory to Describe Partitioning-Driven Processes, Ch. 5, "Prodrugs: Topical and Ocular Drug Delivery" (Marcel Dekker, 1992), and at places elsewhere in the text. All of these references are incorporated herein for the sole purpose of illustrating the level of knowledge and skill in the art concerning drug delivery techniques.

A colloidal dispersion system may be used for targeted delivery of immunomodulatory nucleic acid molecules to specific tissue. Colloidal dispersion systems include macromolecule complexes, nanocapsules, microspheres, beads, and lipid-based systems including oil-in-water emulsions, micelles, mixed micelles, and liposomes.

Liposomes are artificial membrane vesicles which are useful as delivery vehicles in vitro and in vivo. It has been shown that large unilamellar vesicles (LUV), which range in size from 0.2–4.0 µm can encapsulate a substantial percentage of an aqueous buffer containing large macromolecules. RNA and DNA can be encapsulated within the aqueous interior and be delivered to cells in a biologically active form (Fraley, et al., (1981) *Trends Biochem. Sci.*, 6:77). The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations. Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

Where desired, targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various well known linking groups can be used for joining the lipid chains to the targeting ligand (see, e.g., Yanagawa, et al., (1988) *Nuc. Acids Symp. Ser.*, 19:189; Grabarek, et al., (1990) *Anal. Biochem.*, 185:131; Staros, et al., (1986) *Anal. Biochem.* 156:220 and Boujrad, et al., (1993) *Proc. Natl. Acad. Sci. USA*, 90:5728). Targeted delivery of immunomodulatory nucleic acid molecules can also be achieved by conjugation of the ISS to the surface of viral and non-viral recombinant expression vectors, to an antigen or other ligand, to a monoclonal antibody or to any molecule which has the desired binding specificity.

Additional Formulation Components

In addition to immunomodulatory nucleic acid molecules, the formulations suitable for treatment or prevention of intracellular pathogen infections according to the present invention can comprise active or inactive components in lieu of or in addition to the components described above. For example, the formulation may comprise anti-pathogenic agents (e.g., antibiotics), particularly where the ISS is administered for treatment of an active infection. In one embodiment, the immunomodulatory nucleic acid molecule is administered with a relevant antigen to further enhance the subject's immune response against one or more species of intracellular pathogen. In another embodiment, the immunomodulatory nucleic acid molecule is administered with one or more mycobacterial antigens. Mycobacterial antigens of interest may include, but are not necessarily limited to, the 65 kDa antigen and antigen 85B of *M. avium* (Velaz-Faircloth, et al. (1999) *Infect. Immun.* 67:4243–4250); the antigen 85B, ESAT-6 and MPT64 of *M. tuberculosis*

(Kamath, et al. (1999) *Infect. Immun.* 67:1702–1707), and *M. tuberculosis* hsp-65 (Bonato, et al. (1998) *Infect. Immun.* 66:169–175).

Kits

The present invention also provides kits for use in the methods described herein. Such kits may include any or all of the following: 1) ISS; 2) a pharmaceutically acceptable carrier (which may be pre-mixed with the ISS) or suspension base for reconstituting lyophilized ISS; 3) additional medicaments; 4) a sterile vial for each ISS and additional medicament, or a single vial for mixtures thereof; 5) device(s) for use in delivering ISS to a host; 6) assay reagents for detecting indicia that the desired immunomodulatory. effects have been accomplished in the subject to which the ISS has been administered and a suitable assay device.

Intracellular Pathogen Infections Amenable to Treatment

The methods and compositions described herein can be used in the treatment or prevention of any of a variety of infections by intracellular pathogens (e.g., viruses, bacteria, protozoa, fungi, and intracellular parasites) in a variety of subjects susceptible to or having such infections. In one embodiment, the intracellular pathogen infection is a mycobacterial infection. Of particular interest is the treatment and/or prevention of infection or disease by *M tuberculosis, M. avium* (or *M. avium-intracellulare*), *M. leprae* (particularly *M. leprae* infection leading to tuberculoid leprosy), *M. kansasii, M. fortuitum, M. chelonae,* and *M. absecessus*. While treatment of humans is of particular interest, the methods of the invention can also be used to prevent intracellular pathogen infection or disease in non-human subjects. For example, *M. avium* causes lymphadenitis in slaughter pigs; *M. paratuberculosis* infection causes a paratuberculosis, a tuberculosis-like disease that can result in great production losses in cattle, sheep and goats; and *M. bovis* is carried by cattle and can cause a tuberculin-like infection in humans.

Immunomodulatory nucleic acid molecules can be administered prophylactically or following onset of disease. Prophylactic therapy can involve administration of immunomodulatory nucleic acid molecules prior to exposure to intracellular pathogen, or can be after exposure, but prior to establishment of infection or disease (e.g., the subject may be colonized by intracellular pathogen, but not exhibit or yet exhibit symptoms associated with disease caused by the intracellular pathogen due to the subject being a carrier or having been exposed to a sub-infectious dose).

The methods and compositions of the invention may be particularly advantageous in the treatment of infection by drug-resistant strains of intracellular pathogen, as well as treatment of intracellular pathogen infections in immuno-compromised hosts.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Methods and Materials

The following procedures are used in the Examples described in detail below. Although some of the methods described below are in common use, the specific protocol used in the Examples below is described in detail where alternative protocols are often employed. Basic procedures such as DNA digestion by restriction enzymes and ligation are not described, as such are well within the skill of the ordinarily skilled artisan and, in some instances, are carried out according to the enzyme or kit manufacturer's instructions.

Mice.

Female C57B1/6 mice (7 to 8 week-old) were purchased from The Jackson Laboratory (Bar Harbor, Maine) and from Charles River Laboratories, Inc. (Wilmington, *M. AVIUM*). Female 129/SvEv mice were purchased from Taconic Laboratories, Germantown, N.Y. The inducible nitric oxide synthetase (iNOS)$^{-/-}$, IL-12 p40$^{-/-}$, TNF-$\alpha^{-/-}$, and NADPH oxidase (gp91phox)$^{-/-}$ knockout mice are on the C57B1/6 background, and were purchased from The Jackson Laboratory. IFN-$\alpha/\beta$ receptor (IFN-$\alpha/\beta$)$^{-/-}$ and IFN-$\gamma$ receptor (IFN-$\gamma$R)$^{-/-}$ (129/EvSv background) knockout mice were obtained from B & K Universal Ltd. (East Yorkshire, United Kingdom).

Reagents and Cytokines.

Endotoxin-free (<1 ng/mg DNA), phosphorothioate single-stranded oligodeoxynucleotides were obtained from Trilink Biotechnologies, San Diego, Calif. The sequence of the ISS was 5'-TGACTGTGAA<u>CGTTCG</u>AGATGA-3' (SEQ ID NO:1). The sequence of the mutated-ODN (M-ODN) was 5'-TGACTGTGAA<u>GGTTAG</u>AGATGA-3' (SEQ ID NO:3). The underlined bases indicate the CpG motif of the polynucleotide or its corresponding 2 base alteration.

Unless otherwise noted, 10 $\mu$g/ml ISS or M-ODN was used. L-tryptophan (L-try) was obtained from Gibco BRL (Grand Island, N.Y.) and DMEM was supplemented with L-try for a final concentration of 66 $\mu$g/ml. 1-methyl-DL-tryptophan (M-try) was purchased from Aldrich Chemicals (Milwaukee, Wis.). Anti-CD3, anti-CD28, anti-CD4, and anti-CD8 monoclonal antibodies as well as monensin and murine recombinant IFN-$\gamma$ were purchased from BD Pharmingen (San Diego, Calif.). Abbott Laboratories (Abbott Park, Ill.) kindly provided Clarithromycin (CLA).

Culture of *M. avium*.

A previously studied *M. avium* strain 13 (Hayashi, et al. (1999) *Infect. Immun.* 67:3558–3565; Meylan, et al. (1990) *Infect. Immun.* 58:2564–2568), isolated from an AIDS patient at UCSD, San Diego, Calif., was used in all experiments. The organism was cultured on Middlebrook 7H11 agar (Difco Laboratories, Detroit, Mich.) with OADC enrichment at 37° C. in the presence of 5% $CO_2$ for two weeks. Transparent colonies were selectively picked and further cultured on Middlebrook 7H11 plates for two more weeks. The resulting colonies, which were predominantly transparent (>90%), were then collected and washed two times with phosphate-buffered saline (PBS). The bacteria were finally resuspended in Middlebrook 7H9 broth (Difco Laboratories) and the $OD_{600}$ of the suspension was adjusted to 0.15–0.2. The suspension was aliquoted and stored at −70° C. until use. The number of organisms/ml of this suspension was determined by the colony forming unit (CFU) assay.

CFU Assay.

The number of CFU in a given sample was determined by colony counting as described previously (Ogata, et al. (1992) *Infect. Immun.* 60:4720–4725). Serial 10-fold dilutions of total cell lysates or tissue homogenates were performed in PBS. 10 µl of each dilution were plated on Middlebrook 7H11 plates supplemented with OADC enrichment. The plates were incubated up to 14 days at 37° C. The number of colonies was counted every alternate day from day 10 onwards until no new colonies appeared. This yielded the number of CFU/10 µl. The number of CFU in each well was then calculated.

Isolation of Human Monocytes.

Monocytes were isolated from normal human buffy coats obtained from the San Diego Blood Bank by Ficoll-Hypaque and Percoll gradient centrifugation (Hayashi, et al. (1997) *Infect. Immun.* 65:5262–5271). Purity of the monocytes by this method was greater than 70%. The monocytes thus isolated were cultured for five to seven days in Iscove's Modified Dulbecco's Medium (BioWhittaker, Walkersville, Md.) supplemented with 10% normal human serum (Irvine Scientific, Santa Ana, Calif.), 2 mM L-glutamine and 50 units/ml penicillin-streptomycin in Teflon beakers to yield human monocyte-derived macrophages (hMDM). These hMDM were further enriched by adherence to the wells of tissue culture plates before use in experiments. Purity of hMDM after the second adherence assessed by esterase staining was >95%. Viability determined by trypan blue exclusion was >97%.

Preparation of Murine Macrophages. Mouse bone marrow-derived macrophages (mBMDM) were prepared from mouse bone marrow using L-cell conditioned media, as described in Martin-Orozco, et al. (1999) *Immunology* 11:1111–1118.

Effect of ISS on Intracellular Growth of *M. avium* In Vitro.

hMDM ($6\times10^4$) were, adhered to the wells of 96-well tissue culture plates for two hours and non-adherent cells were removed by washing with warm RPMI-1640. Adherent cells were treated with ISS at 3, 10, or 30 µg/ml for 72 h before infection with *M. avium*. Cells treated with M-ODN at 10 µg/ml or with media alone served as controls. After 72 h, the cells were washed two times and infected with *M. avium* in RPMI-1640 supplemented with 5% heat-inactivated fetal bovine serum (FBS, Irvine Scientific) at a cell:bacteria ratio of 1:5–1:10. On days 1, 3 and 7 after infection, the total number of colony forming units (CFU) in each well was determined. The supernatant was collected and set aside and the adherent cells were lysed. To account for all the mycobacteria in each well, corresponding lysates and supernatants were combined and used to determine the number of CFU. Experiments were done in triplicate and results were expressed as mean±SD of CFU per well.

Alternatively, $5\times10^4$ mBMDM or hMDM was treated with ISS for 3 days before infection. Macrophages treated with M-ODN or with media alone served as controls. After 3 days, the cells were infected for 2 hrs with *M. avium* at a macrophage:bacteria ratio of 2:1 for mBMDM or of 1:10 for hMDM, and subsequently cultured in fresh media without antibiotics. To examine attachment and/or invasion of *M. avium*, the macrophages were lysed immediately after washing, and the number of bacteria were enumerated by the CFU assay. Intracellular growth of *M. avium* was determined on days 1, 3 and 7 after infection. To account for all the mycobacteria in each group, corresponding lysates were combined and then the number of CFU was determined. To examine the efficacy of anti-mycobacterial treatments, CFU recovered from cells treated with medium alone were considered as 100% growth.

To determine whether treatment with ISS after infection alters *M. avium* growth, adherent cells were first infected with *M. avium* for 2 hrs and then these cells were cultured with fresh media containing ISS. Infected cells treated with M-ODN or medium alone served as controls. At day 7, intracellular growth of *M. avium* was assessed by CFU assay.

Effect of ISS on Growth of *M. avium* In Vivo in Mice.

Three days before infection, the experimental mice (n=5) were injected intradermally with ISS (100 µg/mouse in 50 µl). The control mice (n=5) received PBS (50 µl/mouse). All mice were infected intravenously with *M. avium* ($1\times10^6$/mouse or $1\times10^7$/mouse). At 2, 4, and 6 weeks after infection, mice were sacrificed and the spleen, liver, and lungs from each mouse were collected and weighed. Blood was collected by cardiac puncture and used in the ELISA studies described below. A section of each organ was minced and homogenized for 30 s with 0.25% SDS in PBS (1 ml/100 mg of tissue). The number of CFU in the tissue homogenates was determined by the CFU assay and the results were expressed as CFU/organ. All procedures were performed under a biosafety cabinet in a biosafety level 2 facility.

To study the effect of ISS when combined with CLA in vivo, 25 mice were injected with *M. avium* ($1\times10^7$/mouse). One week after infection, treatment with either ISS or M-ODN and CLA was initiated. The mice were divided into 5 treatment groups (n=5 per group): group 1, no treatment; group 2, ISS alone; group 3, CLA alone; group 4, CLA and ISS; and group 5, CLA and M-ODN. CLA (200 mg/kg) was administered intraperitoneally three times a week for four weeks (Doherty, et al. (1998) *J. Immunol.* 160:5428–5435) and bacterial growth in the spleen, liver and lungs was determined.

Intracellular IFN-γ Staining and Detection of Secreted IFN-γ by ELISA.

Mice were injected intradermally (i.d.) with ISS (50 µg/mouse). The control mice received M-ODN (50 µg/mouse) or PBS (50 µl/mouse). All mice were infected with $1\times10^7$ *M. avium*. Three weeks after infection, the mice were sacrificed and splenocytes from mice receiving the same treatment were pooled. Intracellular cytokine staining was performed using the Cytofix/Cytoperm kit (Pharmingen) according to the manufacturer's instructions. Briefly, the splenocytes were stimulated with anti-CD3 and anti-CD28 activating antibodies in the presence of monensin to allow intracellular IFN-γ to accumulate for 6 hrs. Next, surface CD4 and CD8 were stained for, the cells were fixed, and the plasma membranes were permeabilized, allowing for intracellular staining with anti-IFN-γ. The cells were analyzed on a FACSCalibur flow cytometer (Becton Dickenson). To study IFN-γ production, splenocytes were incubated with anti-CD3 and anti-CD28 antibodies in vitro for 24 hrs, and these supernatants were assayed for the presence of IFN-γ by sandwich ELISA (Martin-Orozco, et al. (1999) *Int. Immun.* 11:1111–1118).

RNA Extraction, RT-PCR, and IDO Activity Assay.

$1-4\times10^6$ mBMDM were treated with ISS or M-ODN. After 3 days, the cells were infected with *M. avium* for 2 hrs. At 2, 24, and 48 hrs after infection, the *M. avium*-infected macrophages were lysed and total RNA was isolated using the Trizol Reagent (Gibco BRL). The induction of IDO gene transcription was measured by semi-quantitative RT-A PCR. First-strand cDNA preparation and PCR amplification was carried out using the SuperScript Pre-amplification System (Gibco BRL) and AdvanTaq Plus DNA polymerase (Clontech, San Francisco, Calif.), respectively. PCR prod ucts were visualized by electrophoresis on 2% agarose gels. The primer sequences used were as follows:

```
IDO:     5'-TTATGCAGACTGTGTCCTGGCAAA-3'
         (SEQ ID NO:4) and

5'-TTTCCAGCCAGACAGATATATGCG-3'
         (SEQ ID NO:5),

G3PDH:   5'-ACCACAGTCCATGCCATCAC-3'
         (SEQ ID NO:6) and

5'-TCCACCACCCTGTTGCTGTA-3'
         (SEQ ID NO:7)
```

IFN-γ and IL-12 Measurement in the Serum of *M. avium*-infected Mice.

Serum obtained from *M. avium*-infected mice that received ISS or PBS was assayed for IFN-γ and IL-12 by ELISA using mouse IFN-γ and IL-12 (p70) ELISA kits (Endogen, Inc. Woburn, *M. AVIUM*), respectively, and following the manufacturer's instructions.

Histologic Examination.

Sections of the spleen and liver collected from the experimental and control *M. avium*-infected mice at 2, 4, and 6 weeks post-infection, were fixed overnight in 10% buffered formalin at room temperature, and embedded in paraffin. The paraffin-embedded tissue was further sectioned (5 μm thickness), stained with hematoxylin-eosin and observed under an Olympus microscope. At least three sections from each organ of each of the experimental and control mice were evaluated and representative fields were viewed at 100×.

Statistical Analysis.

Results were expressed as mean±SD. Statistical differences were determined using the Student's t test (two-tailed distribution). A P value at or below 0.05 was considered to be statistically significant.

Example 1

In Vitro Effect of ISS on the Growth of *M. avium* in Human MDM

To examine whether ISS has a direct effect on the growth of *M. avium* in human monocyte-derived macrophages (hMDM), hMDM were prepared as described above ($6\times10^4$ hMDM/well) and pretreated with ISS or M-ODN for 72 h before infection and then infected with *M. avium*. The number of CFU within the cells was determined on days 1, 3 and 7 post-infection.

On day 7, maximum inhibition of intracellular growth of *M. avium* was observed in the case of hMDM pretreated with 3 μg/ml of ISS (91.3±1.7%) in comparison with hMDM treated with medium alone or those treated with M-ODN (p<0.001) (FIG. 1). There was no further increase in growth inhibition at the higher concentrations of ISS tested. These results demonstrate that ISS can directly stimulate macrophages to restrict the intracellular growth of *M. avium*.

In summary, these data show that pretreatment of hMDM with ISS significantly inhibited the intracellular growth of *M. avium* for up to 7 days, demonstrating that ISS may directly activate macrophages to kill *M. avium*.

Example 2

Effect of Treatment with ISS Upon Infected HMDM.

To study the effect of ISS upon growth of *M. avium* in an on-going infection of hMDM, hMDM were infected as described above ($6\times10^4$ hMDM/well) and incubated with ISS (10 mg/ml) either immediately after infection, or one day after infection. In some wells hMDM were pretreated with ISS (10 mg/ml) three days before infection and were then infected with *M. avium* as described above. CFU of these wells was determined at day 7. Experiments were done in triplicate and results were expressed as mean±SD of CFU per well.

Figure 2:
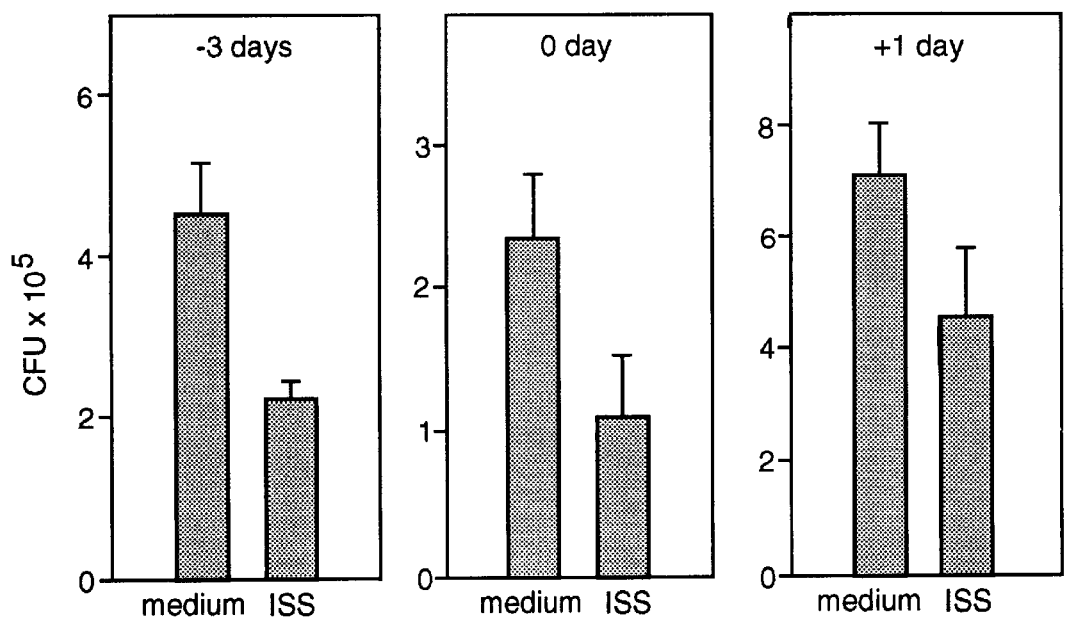
FIG. 2 is a graph showing the effect of ISS upon infected hMDM. ISS, ISS added; medium, medium alone.

Pretreatment of ISS three days before infection (−3 days) inhibited intracellular growth of *M. avium* 51±4% compared to medium alone as the control (FIG. 2). Treatment with ISS immediately after infection (0 day) and one day after infection (+1 day) inhibited growth of *M. avium* 53±18% and 36±16%, respectively. These data indicate that treatment with ISS after infection can also activate hMDM to inhibit *M. avium* growth as well as pretreatment with ISS.

Example 3

Effect of ISS upon *M. avium* Infection in the Presence of Antibiotics

In order to assess whether ISS would work effectively with other anti-mycobacterial agents, the effect of ISS and the antibiotic clarithromycin (ZITHROMAX®, Pfizer Labs, New York, N.Y.) were coadministered to *M. avium*-infected hMDM and intracellular growth of *M. avium* was evaluated. *M. avium*-infected hMDM were prepared as described above ($6\times10^4$ hMDM/well), and then incubated with ISS (10 μg/ml) in the presence or absence of 1 μg/ml, 4 μg/ml, or 20 μg/ml clarithromycin, an antibiotic used to treat *M. avium* infection. CFU was determined on days 0 and 7 after infection. The experiment was done in triplicate and results expressed as mean±SD of CFU per well.

Figure 3:
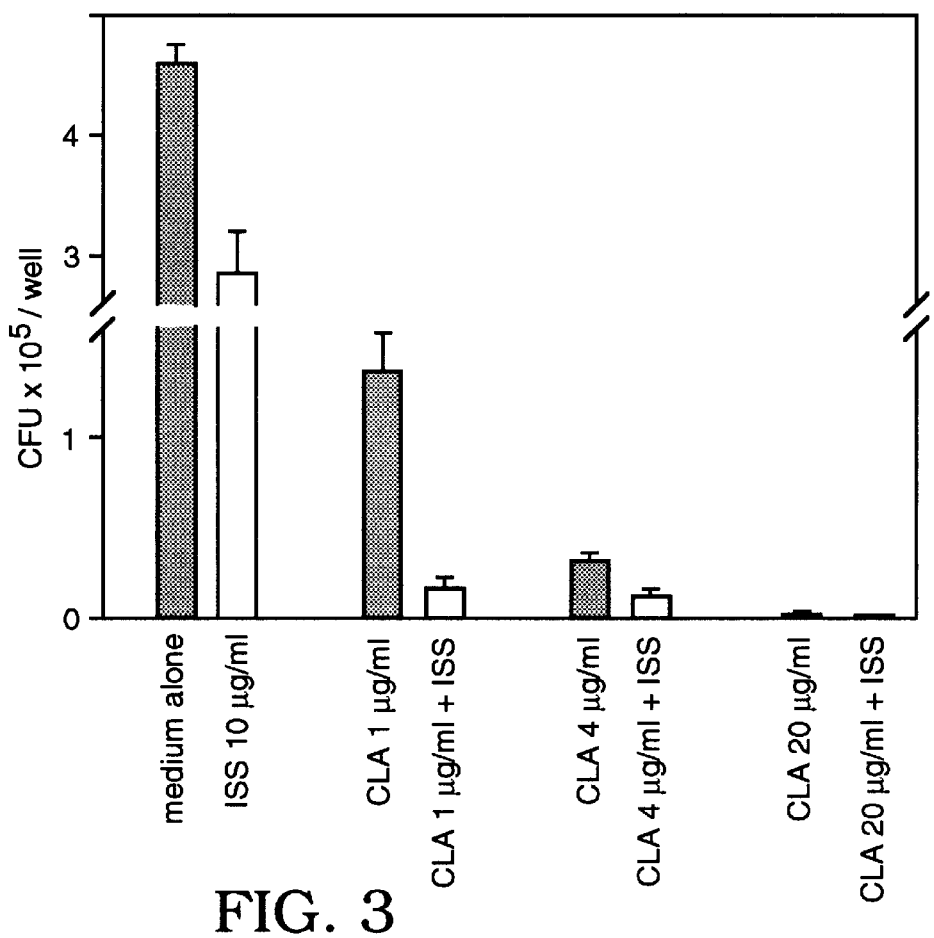
FIG. 3 is a graph showing the effect of ISS and antibiotics upon infected hMDM. ISS, ISS; CLA, clarithromycin.

On day 7, ISS alone inhibited intracellular growth of *M. avium* by 38±7% (p=0.05) (FIG. 3). ISS further enhanced the anti-mycobacterial effect of 1 μg/ml and 4 μg/ml clarithromycin by 89±5% (p<0.001) and 63±12% (p=0.001), respectively, compared to antibiotic alone. These data show that ISS and clarithromycin had a synergistic effect in inhibition of *M. avium* replication.

Figure 4A:
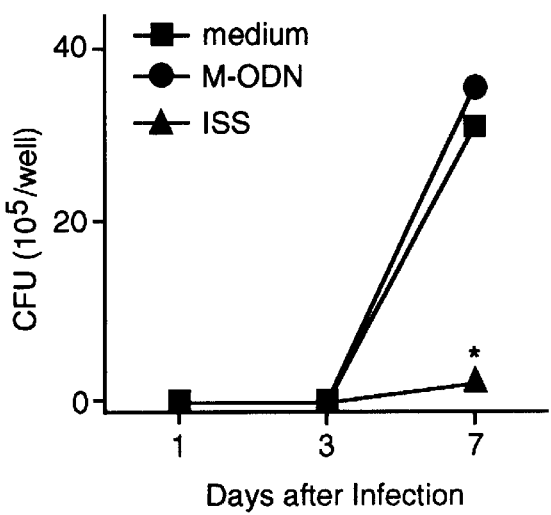
FIGS. 4A–4B are graphs showing the effect of ISS, exemplified here by ISS-ODN, on intracellular growth of M. avium in hMDM in vitro (FIG. 4A) and effect of ISS and antibiotics upon infected hMDM (FIG. 4B). Closed square, medium alone; closed circle, mutated ISS; closed triangle, ISS. ISS, ISS-ODN; M-ODN, mutated-ODN; CLA, clarithromycin. Results shown are mean±SD for three experiments. *p<0.01 compared to CFU recovered from cells treated with M-ODN or medium alone.
Figure 4B:
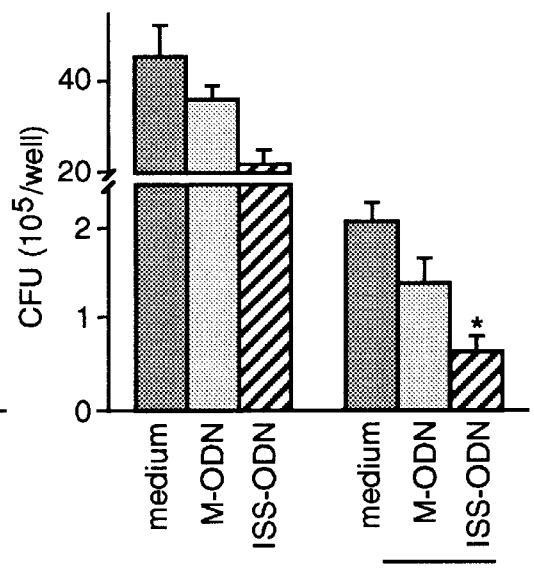

In another experiment, hMDM ($5\times10^4$ hMDM/well) were treated with ISS or M-ODN (3, 10, and 30 μg/ml) for 3 days and then infected them with *M. avium*. There was maximal inhibition of *M. avium* growth at 3 μg/ml of ISS (FIG. 4A) with no further increase in inhibition at the higher concentrations (data not shown). At 7 days post-infection, treatment with ISS was found to have inhibited intracellular growth of *M. avium* by 91% (FIG. 4A, p<0.001). No changes in cell viability in the various groups was observed. To study the therapeutic effects of ISS on established *M. avium* infection, infected hMDM were treated with ISS (10 μg/ml) for 7 days. Treatment with ISS significantly decreased the intracellular growth of *M. avium* in hMDM by 53% (p<0.05) (FIG. 4B). When infected cells were treated with ISS together with CLA (0.5 μg/ml), *M. avium* growth was further inhibited up to 99% (p<0.01), compared to medium alone (FIG. 4B).

Example 4

Figure 5A:
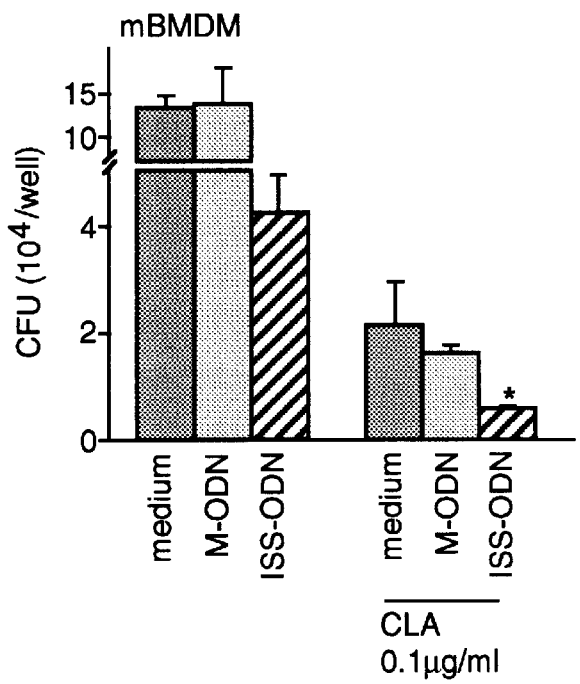
FIGS. 5A–5C are graphs showing the effect of ISS and antibiotics on mBMDM in vivo (FIG. 5A) and in vitro (FIGS. 5B–5D). Results shown are mean±SD for three experiments. *p<0.05 compared to CFU in the organs of control mice that received CLA only or a combination of CLA and M-ODN.

ISS is a Potent Adjunct to Anti-mycobacterial Therapy with CLA.

mBMDM ($5\times10^4$ mBMDM/well) was first infected with *M. avium* and then these cells were treated with CLA (0. I Vg/ml) in the presence or absence of ISS (10 μg/ml) or M-ODN (10 μg/ml) and *M. avium* growth in vitro 7 days after infection was determined. ISS and CLA (0.1 μg/ml), when used individually, reduced bacterial growth in mBMDM by 68% and 84%, respectively (p<0.01, FIG. 5A). When ISS was used together with CLA, bacterial counts were further reduced (95%, p<0.01) compared to medium alone (FIG. 5A).

Figure 5B:
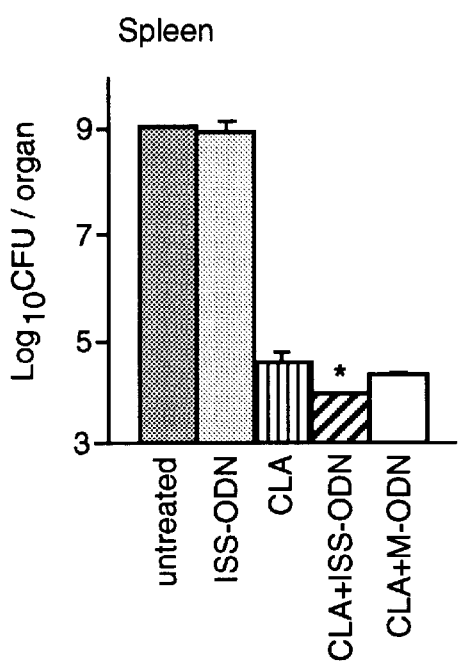
Figure 5C:
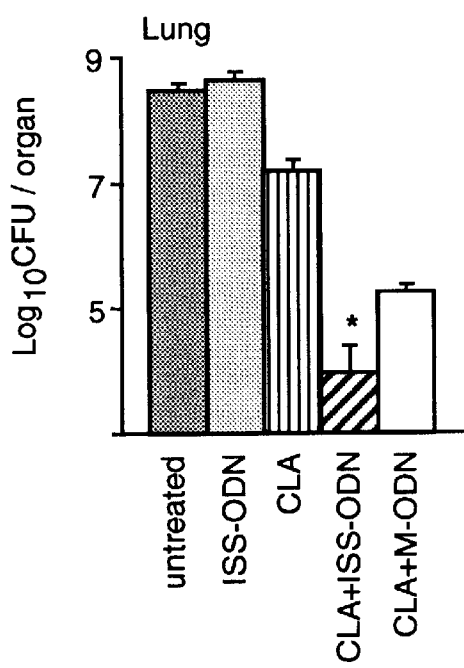
Figure 5D:
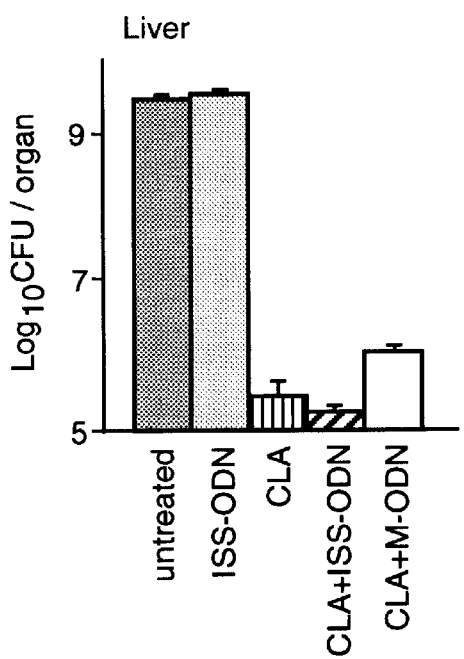

C57B1/6 mice were infected intravenously with *M. avium* ($10^7$ CFU) and were treated with a combination of ISS-ODN (50 μg/mouse) and/or CLA (200 mg/kg) one week after infection. Mice were sacrificed 5 weeks after infection and CFU in the spleen, liver, and lungs were counted. Treatment with CLA alone decreased bacterial growth in the spleen (4 log reduction, FIG. 5B), liver (4 log reduction, FIG. 5D) and lungs (1.5 log reduction, FIG. 5C). In this therapeutic model, ISS alone did not inhibit the growth of *M. avium*. However, when ISS was combined with CLA, there was a further reduction of bacterial counts in the spleen (<1 log reduction, p<0.01, FIG. 5B) and especially in the lungs (3 log reduction, p<0.01, FIGS. 5B–5D). These findings show that ISS can enhance the therapeutic efficacy of CLA in the setting of established *M. avium* infection.

Example 5

In Vivo Effect of ISS on *M. avium* Infection in Mice

The ability of ISS to elicit a protective immune response against mycobacterial infection was tested in an animal model of disseminated mycobacterial infection. C57B1/6 mice were pretreated intradermally with ISS and subsequently infected with $10^6$ or $10^7$ organisms/mouse as described in the Materials and Methods above.

a) Bacterial Load

At 2, 4 and 6 weeks after infection, the spleen, liver, and lungs were collected from the *M. avium*-infected mice ($10^6$ organisms/mouse), homogenized and used to determine the number of CFU as described in Materials and Methods above.

Figure 6:
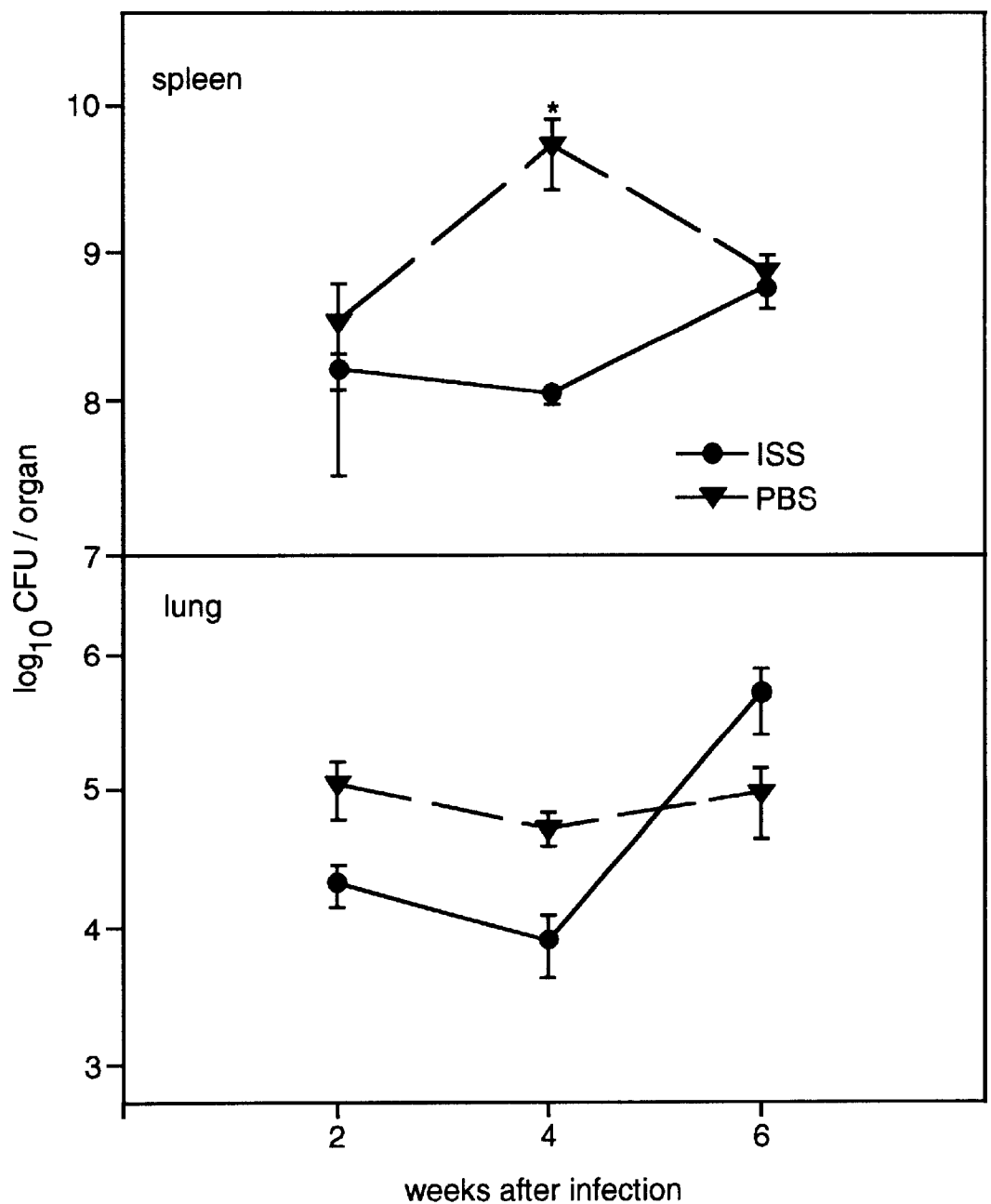
FIG. 6 is a graph showing the effect of ISS, exemplified here by ISS-ODN, on M. avium ($10^6$ organisms/mouse) growth in C57B1/6 mice. Results shown are mean±SD of the number of CFU per organ (spleen, top panel; lung, bottom panel). ISS, closed circles; PBS (control), triangles and dashed lines. *p<0.05 compared to CFU in the organs of control mice that received PBS instead of ISS. Results shown are mean±SD.

At week 2, the lungs of *M. avium*-infected mice pretreated with ISS were found to contain a significantly lower number of viable bacteria compared to those of infected mice which received PBS instead of ISS (p<0.05). In addition, *M. avium*-infected mice pretreated with ISS were found to have an almost two logs lower number of bacteria in the spleen (p<0.05) compared to the PBS-pretreated mice (FIG. 6). These effects were maximal at 4 weeks. At week 6, CFU in the spleen of mice treated with ISS equaled that observed in the control mice treated with PBS. Surprisingly, at week 6 the bacterial load in the lungs of ISS-treated mice exceeded that found in the lungs of control mice (FIG. 6). This observation suggests that ISS alone does not eradicate the mycobacterial infection under the conditions described.

There was no significant difference in the bacterial loads in the liver of mice pretreated with ISS compared to those recovered from mice pretreated with PBS at any of the time points (data not shown). Thus, a single injection of ISS significantly reduced the mycobacterial growth in the spleen and the lungs, but not in the liver in *M. avium*-infected mice. This protective effect was found to persist for up to four weeks after administration of ISS. These data demonstrate that ISS by itself can induce strong protective immunity against mycobacterial infections even in the absence of specific DNA sequences which code for mycobacterial antigens.

In another experiment, mice were treated with ISS and infected intravenously (i.v.) three days later with *M. avium* ($10^7$ organisms/mouse). At 2, 4, and 6 weeks after infection, the number of CFU in the spleen, lungs, and liver were determined. Four weeks after infection, CFU in the spleen and lungs were similar in the mice treated with M-ODN and control (PBS) mice, but were significantly higher than in the ISS-treated mice (by 2 logs and 1 log in spleen and lungs, respectively).

Figures 7A, 7B, 7C:
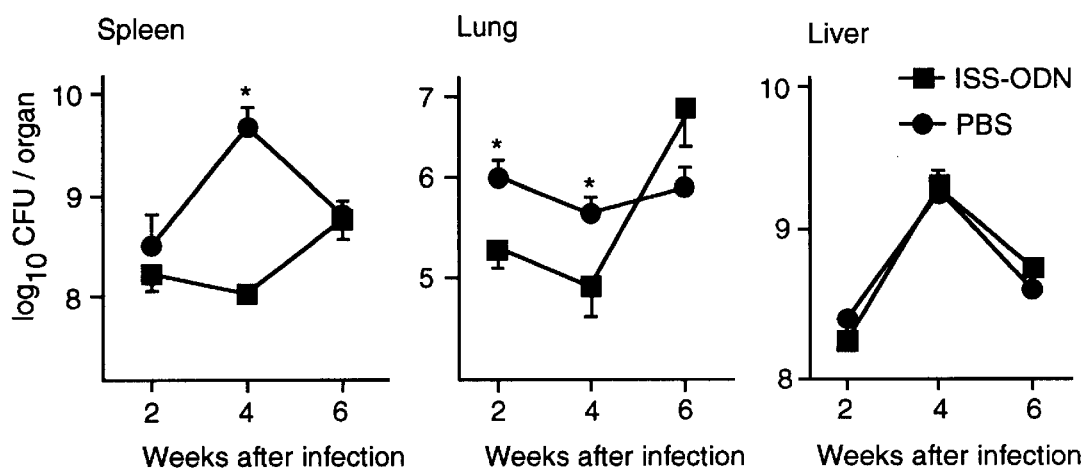
FIGS. 7A–7C are graphs showing the effect of ISS, exemplified here by ISS-ODN, on M. avium ($10^7$ organisms/mouse) growth in C57B1/6 mice. Results shown are mean±SD of the number of CFU per organ (spleen, FIG. 7A; lung, FIG. 7B; liver, FIG. 7C). ISS, closed circles; PBS (control), triangles and dashed lines. *p<0.05 compared to CFU in the organs of control mice that received PBS instead of ISS. Results shown are mean±SD.

At week 2, the lungs of *M. avium*-infected mice treated with ISS prior to infection contained a significantly lower number of viable bacteria compared to control PBS-treated mice (p<0.05) (FIG. 7B). In addition, mice treated with ISS prior to *M. avium* infection had nearly two logs less bacteria in the spleen at 4 weeks (p<0.05) compared to the PBS-treated mice (FIG. 7A). By 6 weeks, however, splenic CFU counts were similar in control and ISS groups. There was no significant difference in the mycobacterial loads in the liver of mice treated with ISS prior to infection compared to PBS-treated mice at any of these time points (FIG. 7C). Thus, a single injection of ISS significantly reduced the mycobacterial growth in the spleen and lungs, but not in the liver of *M. avium*-infected mice. This protective effect was transient and was most apparent at 2 and 4 weeks after a single administration of ISS.

b) Serum IFN-γ and IL-12 Levels.

Figure 8:
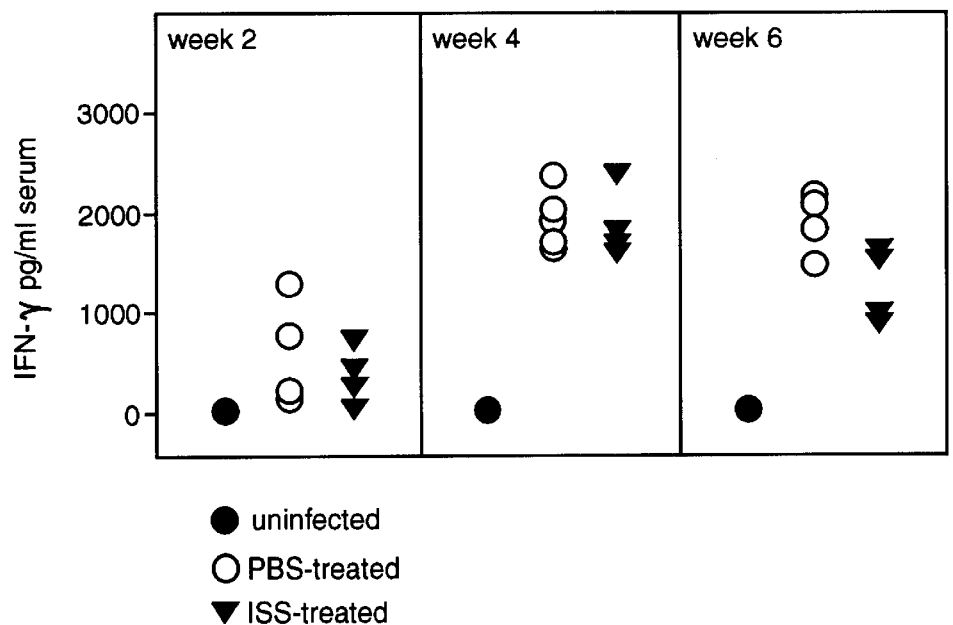
FIG. 8 is a graph showing IFN-γ production in M. avium-infected mice pre-treated with ISS, exemplified here by ISS-ODN. Levels at weeks 2, 4, and 6 are shown in left, center, and right panels, respectively. Uninfected, closed circles; PBS-treated control, open circles; ISS-ODN treated, closed triangles.

To determine whether production of IFN-γ and IL-12 could be responsible for the protective effect exerted by ISS, serum was collected from the ISS-treated or PBS-treated *M. avium*-infected mice ($10^6$ organisms/mouse) at 2, 4, and 6 weeks after infection. Serum IFN-γ levels of mice infected with *M. avium* was found to be significantly higher than that of uninfected mice throughout the experiment (p<0.05) (FIG. 8). However, there were no significant differences in the serum IFN-γ levels of ISS-pretreated mice compared to PBS-pretreated mice. Serum IL-12 levels were found to be less than that detectable by the ELISA (<5 pg/ml).

In other experiments not described here, the serum level of IFN-γ and IL-12 after administration of ISS peaks at day 1, after which levels begin to decline and attain basal levels within 3 weeks post injection (data not shown) (see, e.g., Kobayashi et al. (1999) *Cell. Immunol.* 198:69–25).

These data indicate that there is no significant difference in serum IFN-γ levels between ISS-treated and PBS-treated infected mice. This could be due to the fact that induction of IFN-γ production is an early event during the course of *M. avium* infection. Our earliest blood samples for IFN-γ assay were collected 2 weeks after infection, by which time the IFN-γ levels may have returned to the basal level. Alternatively, *M. avium* may induce IFN-γ production as efficiently as ISS so no differences would be observed. Serum IL-12 (p70) was found to be undetectable at all the time points of the experiment (2, 4 and 6 weeks). In studies by other investigators, total IL-12 (p40 and p70) was measured, whereas in our study, only biological-active IL-12 p70 was measured, which may explain the disparity in observations.

c) Histology.

Tissue sections from the spleen of *M. avium*-infected mice treated with ISS, PBS or uninfected mice were fixed and stained with hematoxylin-eosin as described in the Materials and Methods above. At week 4, the white pulp in the spleen from *M. avium*-infected mice treated with PBS was disrupted with the formation of several granulomas, while the white pulp in the spleen of the uninfected mice was intact. Sections of the spleen from the ISS-treated mice also revealed the presence of granulomas, although they were notably smaller in size and surrounded by mononuclear cells in contrast to the spleens from infected mice treated with PBS.

The red pulp in spleens of ISS-treated mice appeared to contain increased hematopoietic cells. However, at week 6, the granulomas in the spleens from ISS-treated, *M. avium*-infected mice were not significantly different from those of PBS-treated, *M. avium*-infected mice correlating well with the CFU data and the loss of effect of ISS observed at this time point (presented above).

Overall, ISS appears to cause a delay in the formation of granulomas, which may be associated with the presence of increased numbers of mononuclear and hematopoietic cells in the spleen. The livers of the *M. avium*-infected mice showed a significant number of granulomas at weeks 4 and 6, while the livers from uninfected mice did not show any granulomas, as expected. However, there were no significant histopathological differences in the livers recovered from the ISS-treated, *M. avium*-infected mice compared to those recovered from PBS-treated, *M. avium*-infected mice (data not shown).

d) Summary

These data show that a significant inhibitory effect by ISS against *M. avium* growth was seen in the spleen and the lungs, but not significantly in the liver. Histopathology studies showed that the spleen of ISS treated, *M. avium*-infected mice contained significantly increased numbers of mononuclear cells compared to the spleen of the PBS-treated, *M. avium*-infected control mice. No significant histopathological differences were observed between the livers recovered from ISS-treated and PBS-treated mice.

Example 6

In Vivo Effect of ISS on the Growth of *M. avium* in Mouse BMDM.

The following studies were performed to address whether ISS-induced activation of macrophages in vitro inhibits intracellular growth of *M. avium*.

a) Treatment Prior to Infection.

Figure 9A:
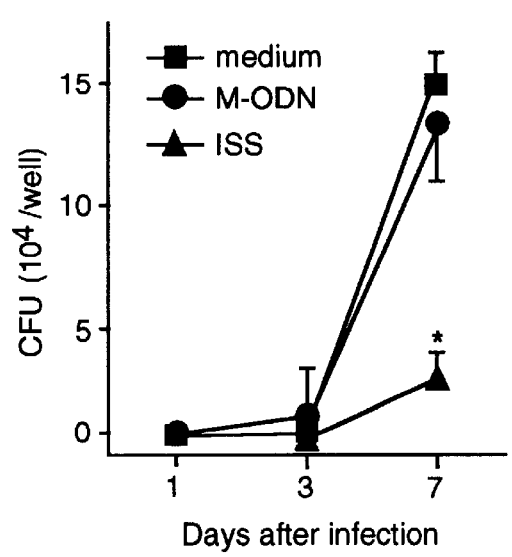
FIGS. 9A–9B are graphs showing the effect of ISS on intracellular growth of M. avium in mBMDM in vitro on days 1, 3, and 7 after infection (FIG. 9A) and 7 days after infection (FIG. 9B). Closed square, medium alone; closed circle, mutated ISS; closed triangle, ISS. Results shown are mean±SD for triplicate experiments. *p<0.01 compared to CFU recovered from cells treated with M-ODN or medium alone.

To examine whether treatment with ISS can stimulate macrophages to inhibit the growth of *M. avium*, mBMDM ($5 \times 10^4$ mBMDM/well) was first treated with ISS or M-ODN for 72 hrs and then infected with *M. avium*. Then, cellular CFU was counted on days 1, 3, and 7 post-infection (FIG. 9A). By day 7, treatment with ISS inhibited intracellular growth of *M. avium* in mBMDM by 80% ($p < 0.001$). Since viability of macrophages can affect *M. avium* growth, the viability of macrophages was assessed by trypan-blue exclusion. At day 7 after infection, MBMDM treated with ISS, M-ODN or medium alone were all >90% viable.

ISS activate macrophages and induce the expression of surface adhesion molecules such as ICAM-1 (Martin-Orozco, et al. (1999) *Int. Immun.* 11:1111–1118). These molecules may affect the attachment of *M. avium* or its invasion into mouse bone marrow-derived macrophages (mBMDM). In order to determine whether the ability of ISS to inhibit *M. avium* growth is due to alterations in susceptibility to *M. avium* invasion, the ability of ISS to influence the number of bacteria that attached to and invaded macrophages after incubation with *M. avium* was examined. CFU recovered immediately from cells treated with ISS before infection were not significantly different than CFU recovered from cells treated with mutated (M)-ODN or with medium alone.

b) Treatment After Infection.

Figure 9B:
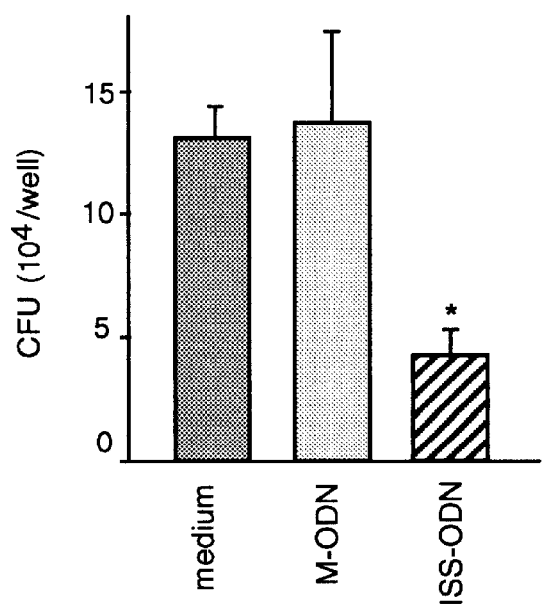

To study the therapeutic anti-mycobacterial effect of ISS, infected mBMDM were treated with ISS for 7 days after infection, starting two hours after time of infection. Treatment with ISS significantly decreased the intracellular growth of *M. avium* in mBMDM by 68% ($p < 0.05$), compared to CFU in infected cells treated with M-ODN or medium alone (FIG. 9B).

Example 7

ISS Protection In Vivo is not Significantly Mediated through Augmentation of the T Cell Response.

Figure 10A:
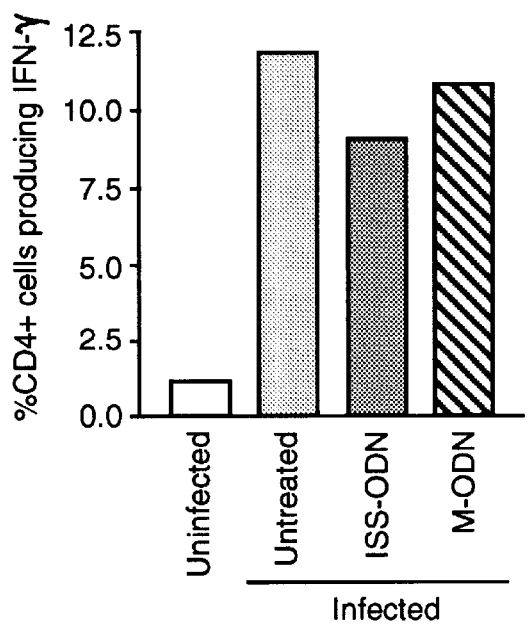
FIGS. 10A–10C are graphs showing the CD4$^+$ (FIG. 10A), CD8$^+$ (FIG. 10B), and IFN-γ$^+$ (FIG. 10C) T cell responses of mice treated with either ISS or M-ODN prior to infection. Splenocytes were pooled within groups for intracellular IFN-γ assays (panels A, B). For total IFN-γ produced, results represent the mean±SD (panel C).
Figure 10B:
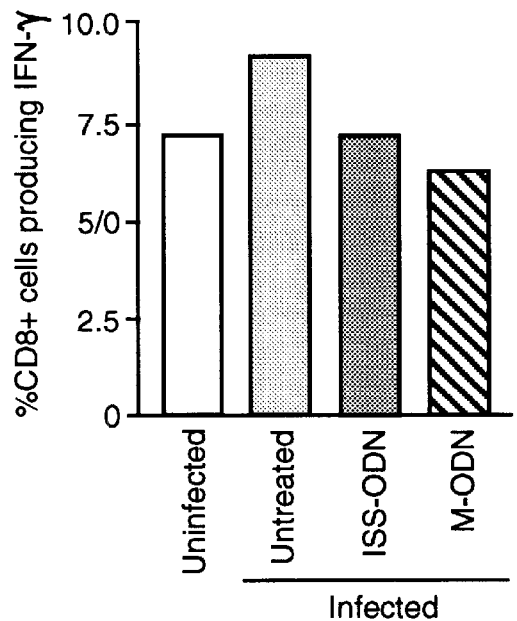
Figure 10C:
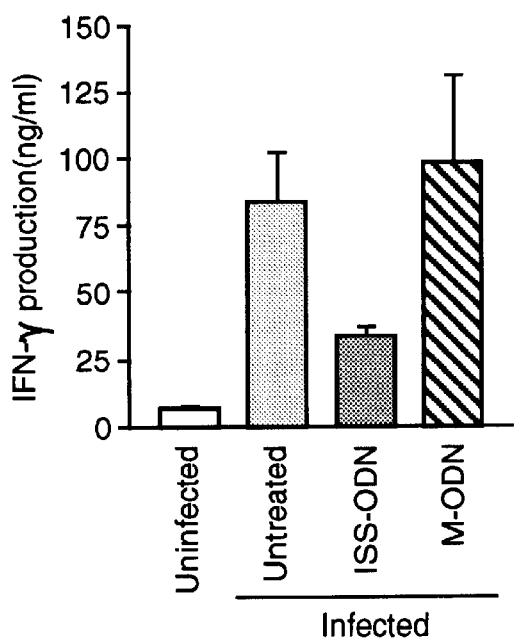

The observations that ISS protects isolated macrophages in vitro (FIG. 9) and that the protective effect observed in ISS-treated mice is transient (FIGS. 6 and 7) suggest a T-cell independent mechanism of protection via innate immunity. To further investigate the potential role of adaptive immunity in this model of ISS-mediated protection against *M. avium*, mice were treated with ISS or M-ODN (50 µg/mouse), infected with $10^7$ organisms/mouse, and then their T-cell response was evaluated. The mice were sacrificed at three weeks post-infection and the splenocytes were re-stimulated with anti-CD3 and anti-CD28 antibodies to amplify the response from pre-existing memory and activated T cells. T cells were then examined for their production of IFN-γ by two complementary methods. FACS-based intracellular cytokine staining was used to determine the frequencies of IFN-γ producing $CD4^+$ (FIG. 10A) and $CD8^+$ (FIG. 10B) T cells, and ELISA was used to determine the total quantity of IFN-γ secreted by $CD4^+$ and $CD8^+$ T cells combined (FIG. 10C). There was a dramatic increase in the IFN-γ response of the $CD4^+$ T cells and in the total IFN-γ produced in the infected vs. uninfected animals, demonstrating that the observed Th1 response is infection-specific. However, treatment of *M. avium*-infected animals with ISS did not further increase the frequency of infection-specific IFN-γ positive $CD4^+$ or $CD8^+$ T cells nor did it increase the secretion of total infection-specific IFN-γ. Taken together, these data suggest that the mechanism of protection by ISS of *M. avium*-infected animals does not involve enhancement of the anti-mycobacterial T-cell response.

Example 8

ISS inhibition of *M. aviuni* Growth in Macrophages is Independent of iNOS, NAPDH Oxidase, IL-12, TNF-α, IFN-α/β, and IFN-γ.

To further investigate the mechanisms of the anti-mycobacterial effects of ISS, mice with targeted disruptions of genes known to play roles in *M. avium* infection were used. Oxygen radicals generated by NADPH oxidase and induction of nitric oxide (NO) by iNOS result in anti-microbial activity against many microorganisms (Miller, et al. (1997) *Clin. Microbiol. Rev.* 10:1–18; Fang (1997) *J. Clin. Invest.* 99:2818–2825). IL-12, TNF-α, and IFN-γ play important roles in the clearance of *M. avium* (Kobayashi, et al. (1995) *Antimicrob. Agents Chemother.* 39:1369–1371; Doherty, et al. (1998) *J. Immunol.* 160:5428–5435; Appelberg, et al. (1995) *Clin. Exp. Immunol.* 101:308–313). Furthermore, macrophages produce IL-12, TNF-α, IFN-α/β, and IFN-γ in response to ISS treatment (Klinman, et al. (1996) *Proc. Natl. Acad. Sci. USA.* 93:2879–2883; Roman, et al. (1997) *Nat. Med.* 3:849–854).

To study the role of these molecules in the anti-mycobacterial effect of ISS, mBMDM from NADPH oxidase$^{-/-}$, iNOS$^{-/-}$, TNF-α$^{-/-}$, IL-12p40$^{-/-}$, IFN-α/βR$^{-/-}$ and IFN-γR$^{-/-}$ mice were treated with ISS for 3 days and then infected with *M. avium*. ISS inhibited the intracellular growth of *M. avium* in mnBMDM from these knockout mice by 60–85% ($p < 0.05$), similar to wild-type mice (Table 1). These results indicate that these gene products (e.g., nitrogen intermediates, oxygen radicals, TNF-α etc.) are not central to the anti-mycobacterial effect induced by ISS in vitro.

TABLE 1

Effect of ISS on *M. avium* growth in mBMDM from mice with targeted disruption of genes known to play a protective role against *M. avium* infection.

| | | % of CFU[a] | | |
|---|---|---|---|---|
| | | | mBMDM were treated with | |
| Mouse | Strain | Untreated | M-ODN | ISS |
| Wild type | C57B1/6 | 100 | 117.2 ± 18.5 | 18.2 ± 7.3[b] |
| Wild type | 129S6/SvEV | 100 | 110.0 ± 15.9 | 17.0 ± 4.0[b] |
| INOS$^{-/-}$ | C57B1/6 | 100 | 105.0 ± 13.9 | 37.3 ± 4.6[b] |
| NADPH oxidase$^{-/-}$ (gp91 phox$^{-/-}$) | C57B1/6 | 100 | 107.0 ± 15.5 | 11.4 ± 1.5[b] |
| TNF-α$^{-/-}$ | C57B1/6 | 100 | 120.0 ± 20.0 | 24.0 ± 6.0[b] |
| IL-12 p40$^{-/-}$ | C57B1/6 | 100 | 117.6 ± 9.2 | 26.4 ± 10.1[b] |
| IFN-αR$^{-/-}$ | 129S6/SvEv | 100 | 106.9 ± 11.9 | 10.9 ± 01.7[b] |
| IFN-γR$^{-/-}$ | 129S6/SvEv | 100 | 108.1 ± 10.8 | 7.6 ± 01.3[b] |

[a]mBMDM were treated with M-ODN or ISS (10 μg/ml) for 72 h prior to infection and then infected with *M. avium*. mBMDM treated with medium alone served as control. On day 7, *M. avium* growth was assessed by CFU assay. For comparison purposes, results are presented as % CFU compared to mBMDM treated with medium alone, rather than absolute CFU in order to normalize for strain variation (i.e. C57B1/6 vs. 129S6/SvEv). CFU of cells treated with medium alone was consideredas 100%. Mean and standard deviations from three independent experiments are shown.
[b]P < 0.05, as compared to mBMDM treated with medium alone.

Example 9

Induction of Indoleamine 2,3-Dioxygenase (IDO) Contributes to the Anti-mycobacterial Activity of ISS.

IDO is the rate-limiting enzyme in the catabolism of tryptophan, which thereby limits the availability of this important amino acid to invading pathogens (Daubener, et al. (1999) *Adv. Exp. Med. Biol.* 467:517–524). To study the potential role of IDO in the anti-mycobacterial effect of ISS, the following were assessed: 1) the induction of IDO activity as measured by semi-quantitative RT-PCR in vivo and in vitro and 2) the abrogation of the anti-mycobacterial effect of ISS by addition of excess L-tryptophan (L-try) or by using a competitive inhibitor for DO, 1-methyl-DL-tryptophan (M-try).

Figure 11A:
FIGS. 11A and 11B are schematics, and FIG. 11C a graph, showing the effect of ISS, exemplified here by ISS-ODN, on indoleamine 2,3-dioxygenase (IDO) in mouse cells.
Figure 11B:
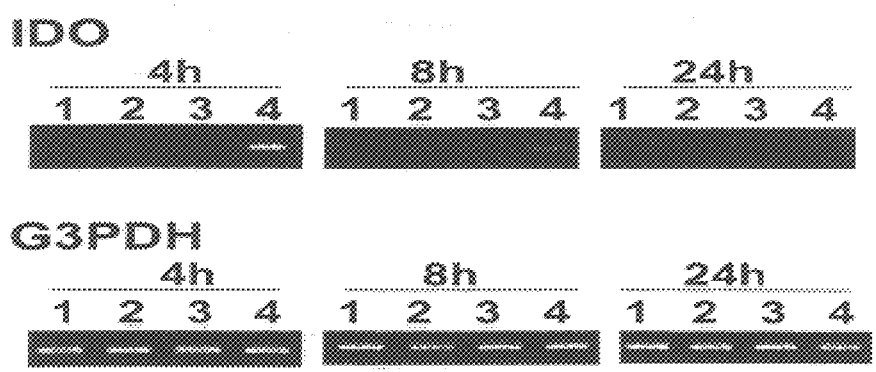

When mice were injected (i.v.) with 50 μg ISS, IDO gene induction in vivo was observed in the lungs and spleen after 16 hrs, but not in the liver (FIG. 11A). Injection of M-ODN did not result in any detectable induction of IDO. For in vitro studies mBMDM were treated with ISS for 3 days prior to *M. avium* infection. Then, cells were lysed at 4, 8, and 24 hrs after infection, total RNA was extracted, and semi-quantitative RT-PCR was performed. Optimal induction of IDO gene transcription was found to require both treatment with ISS and *M. avium* infection (FIG. 11B).

Figure 11C:
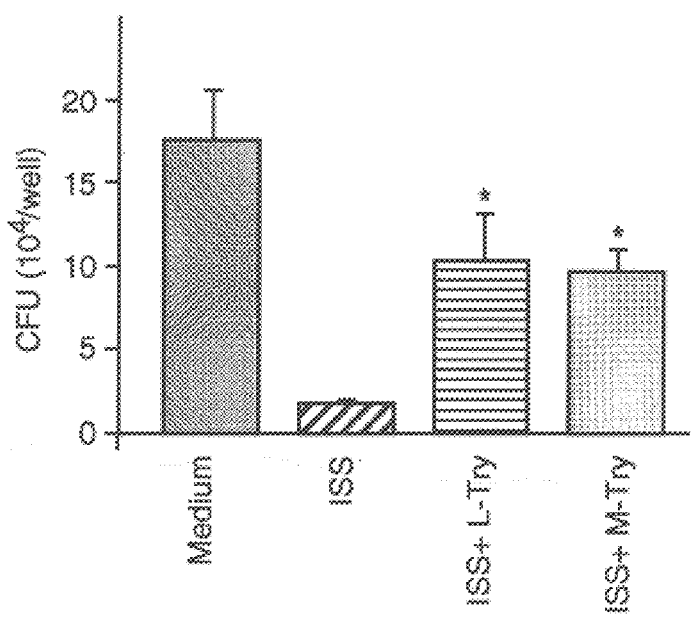
FIG. 11C represents inhibition of ISS induction of IDO by L-tryptophan or 1-methyl-DL-tryptophan (a competitive IDO inhibitor). L-Try, L-tryptophan; M-Try, 1-methyl-DL-tryptophan. Results shown are mean±SD for triplicate experiments. *p<0.01 compared to CFU recovered from cells treated with ISS-ODN.

In order to further investigate the role of IDO in the inhibition of *M. avium* growth, mBMDM were cultured with the IDO inhibitor M-try (125 μM) or with excess L-try (final concentration of 66 μg/ml) (Hwu,et al. (2000) *J. Immunol.* 164:3596–3599; Munn, et al. (1999) *J. Exp. Med.* 189:1363–1372). Addition of L-try or M-try alone at these concentrations did not alter the viability of mBMDM or *M. avium* growth in these cells. However, when the *M. avium*-infected cells were cultured with L-try or M-try supplemented media, 4-fold reductions in the anti-mycobacterial ability of ISS treatment (p<0.05) was observed (FIG. 11C). Taken together, these data show that IDO plays a major role in the observed anti-mycobacterial properties of ISS.

IDO inhibits the growth of a variety of intracellular organisms such as Toxoplasma gondi (Pfefferkorn, et al. (1984) *Infect. Immun.* 44:211–216), Plasmodium berghe in a murine model of malaria (Sanni, et al. (1998) *Am. J. Pathol.* 152:611–619), Chlamydia psittaci (Carlin, et al. (1989) *J. Interferon Res.* 9:329–337), and Chlamydia trachomatis (Beatty, et al. (1994) *Infect. Immun.* 62:3705–3711) by breaking the L-tryptophan required for their growth down to L-kynurenine. IDO has been described to be the most effective anti-parasitic mechanism in most human cells (Daubener, et al. (1999) *Med. Micro. Immunol.* 187:143–147), indicating the broad applicability of ISS for treatment of infection by a wide variety of intracellular pathogens. The anti-pathogenic effects of immunomodulatory nucleic acids such as ISS may induce other anti-pathogen pathways in the host in addition to induction of IDO.

In summary, this study demonstrates that administration of ISS enhances resistance against *M. avium* infection through the induction of IDO. The ISS itself provides protection against *M. avium*. However this effect can be amplified upon co-delivery with an anti-mycobacterial drug, Clarithromycin. The combined administration of ISS with other antibiotics or anti-pathogenic agents provides an alternative therapeutic strategy for intracellular pathogen infections.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A method for treating mycobacterial infection in a subject, the method comprising:
   administering to a subject an immunomodulatory nucleic acid molecule in an amount effective to inhibit intracellular replication of the mycobacterium, wherein the immunomodulatory nucleic acid comprises an immunostimulatory sequence comprising 5' CpG 3'; and
   administering to the subject an anti-pathogenic agent in an amount effective to decrease or inhibit growth of the mycobacterium,
   thereby treating the infection.

2. The method of claim 1, wherein the immunomodulatory nucleic acid molecule is selected from the group consisting of an immunostimulatory oligodeoxyribonucleotide (ISS-ODN); an isolated, detoxified bacterial polynucleotide; and an ISS-enriched plasmid DNA.

3. The method of claim 1, wherein the immunomodulatory nucleic acid molecule comprises a CpG motif selected from the group consisting of:
   a) 5' purine-purine-C-G-pyrimidine-pyrimidine 5';
   b) 5'-Purine-TCG-Pyrimidine-Pyrimidine-3';
   c) 5' (TCG)$_n$3', where n is any integer that is 1 or greater;
   d) 5'-Purine-Purine-CG-Pyrimidine-Pyrimidine-CG-3'; and
   e) 5'-Purine-TCG-Pyrimidine-Pyrimidine-CG-3'.

4. The method of claim 1, wherein the immunomodulatory nucleic acid molecule comprises a sequence selected from the group consisting of: AACGCC, AACGCT, AACGTC, AACGTT, AGCGCC, AGCGCT, AGCGTC, AGCGTT, GACGCC, GACGCT, GACGTC, GACGTT, GGCGCC, GGCGCT, GGCGTC, GGCGTT, ATCGCC, ATCGCT, ATCGTC, ATCGTT, GTCGCC, GTCGCT, GTCGTC, GTCGTT, TCGTCG, TCGTCGTCG, AACGCCG, AACGCTCG, AACGTCCG, AACGTTCG, AGCGCCG, AGCGCTCG, AGCGTCCG, AGCGTTCG, GACGCCG, GACGCTCG, GACGTCCG, GACGTTCG, GGCGCCG, GGCGCTCG, GGCGTCCG, GGCGTTCG, ATCGCCG, ATCGCTCG, ATCGTCCG, ATCGTTCG, GTCGCCG, GTCGCTCG, GTCGTCCG, and GTCGTTCG.

5. The method of claim 4, wherein the immunomodulatory nucleic acid molecule comprises the sequence AACGTTCG.

6. The method of claim 1, wherein the immunomodulatory nucleic acid molecule is administered in an amount effective to provide synergistic anti-pathogenic activity with the anti-pathogenic agent.

7. The method of claim 1, wherein the immunomodulatory nucleic acid molecule and the anti-pathogenic agent are administered concurrently.

8. The method of claim 1, wherein the mycobacterium is selected from the group consisting of *Mycobacterium tuberculosis* and *Mycobacterium avium*.

9. The method of claim 1, wherein said administering of the immunomodulatory nucleic acid enhances indoleamine 2,3-dioxygenase activity in the subject.

10. The method of claim 1, wherein the subject is immunocompromised.

11. The method of claim 10, wherein the immunocompromised subject has a reduced number of CD4+ T cells relative to an immunocompetent subject.

12. A method for treating a mycobacterial infection in a subject, the method comprising:
   administering to a subject multiple doses of an immunomodulatory nucleic acid molecule in an amount effective to inhibit replication of a Mycobacterium bacterium, thereby treating the mycobacterial infection in the subject, wherein the immunomodulatory nucleic acid comprises an immunostimulatory sequence comprising 5' CpG 3'.

13. The method of claim 12, wherein the immunomodulatory nucleic acid molecule is selected from the group consisting of an immunostimulatory oligodeoxyribonucleotide (ISS-ODN); an isolated, detoxified bacterial polynucleotide; and an ISS-enriched plasmid DNA.

14. The method of claim 12, wherein the immunomodulatory nucleic acid molecule comprises a CpG motif selected from the group consisting of:
   a) 5'-Purine-Purine-C-G-Pyrimidine-Pyrimidine-3';
   b) 5'-Purine-TCG-Pyrimidine-Pyrimidine-3';
   c) 5'-(TCG)n-3', where n is any integer that is 1 or greater;
   d) 5'-Purine-Purine-CG-Pyrimidine-Pyrimidine-CG-3'; and
   e) 5'-Purine-TCG-Pyrimidine-Pyrimidine-CG-3'.

15. The method of claim 12, wherein the immunomodulatory nucleic acid molecule comprises a sequence selected from the group consisting of: AACGCC, AACGCT, AACGTC, AACGTT, AGCGCC, AGCGCT, AGCGTC, AGCGTT, GACGCC, GACGCT, GACGTC, GACGTT, GGCGCC, GGCGCT, GGCGTC, GGCGTT, ATCGCC, ATCGCT, ATCGTC, ATCGTT, GTCGCC, GTCGCT, GTCGTC, GTCGTT, TCGTCG, TCGTCGTCG, AACGCCG, AACGCTCG, AACGTCCG, AACGTTCG, AGCGCCG, AGCGCTCG, AGCGTCCG, AGCGTTCG, GACGCCG, GACGCTCG, GACGTCCG, GACGTTCG, GGCGCCG, GGCGCTCG, GGCGTCCG, GGCGTTCG, ATCGCCG, ATCGCTCG, ATCGTCCG, ATCGTTCG, GTCGCCG, GTCGCTCG, GTCGTCCG, and GTCGTCG.

16. The method of claim 15, wherein the immunomodulatory nucleic acid molecule comprises the sequence AACGTTCG.

17. The method of claim 12, wherein said administering results in induction of an immune response effective against infection by a mycobacterial pathogen.

18. The method of claim 12, further comprising administering an anti-pathogenic agent.

19. The method of claim 18, wherein the immunomodulatory nucleic acid molecule is administered in an amount effective to provide synergistic anti-pathogenic activity with the anti-pathogenic agent.

20. The method of claim 18, wherein the immunomodulatory nucleic acid molecule and the anti-pathogenic agent are administered concurrently.

21. The method of claim 12, wherein the bacterium is *Mycobacterium tuberculosis*.

22. The method of claim 12, wherein the bacterium is *Mycobacterium avium*.

23. The method of claim 12, wherein the subject is immunocompromised.

24. The method of claim 23, wherein the immunocompromised subject has a reduced number of CD4+ T cells relative to a immunocompetent subject.

25. A method for inducing in a subject an immune response against a Mycobacterium bacterium, the method comprising:
   administering to a subject multiple doses of an immunomodulatory nucleic acid molecule in an amount effective to elicit an immune response against a Mycobacterium bacterium, wherein the immunomodulatory nucleic acid comprises an immunostimulatory sequence comprising 5' CpG 3';

wherein said administering results in induction of an immune response effective to protect the subject against onset of disease or to decrease severity of symptoms of disease caused by infection by the Mycobacterium bacterium.

26. The method of claim 25, wherein the immunomodulatory nucleic acid molecule comprises a CpG motif selected from the group consisting of:

a) 5'-Purine-Purine-C-G-Pyrimidine-Pyrimidine-3';

b) 5'-Purine-TCG-Pyrimidine-Pyrimidine-3';

c) 5'-(TCG)n-3', where n is any integer that is 1 or greater;

d) 5'-Purine-Purine-CG-Pyrimidine-Pyrimidine-CG-3'; and e) 5'-Purine-TCG-Pyrimidine-Pyrimidine-CG-3'.

27. The method of claim 25, wherein the immunomodulatory nucleic acid molecule comprises a sequence selected from the group consisting of: AACGCC, AACGCT, AACGTC, AACGTT, AGCGCC, AGCGCT, AGCGTC, AGCGTT, GACGCC, GACGCT, GACGTC, GACGTT, GGCGCC, GGCGCT, GGCGTC, GGCGTT, ATCGCC, ATCGCT, ATCGTC, ATCGTT, GTCGCC, GTCGCT, GTCGTC, GTCGTT, TCGTCG, TCGTCGTCG, AACGCCCG, AACGCTCG, AACGTCCG, AACGTTCG, AGCGCCCG, AGCGCTCG, AGCGTCCG, AGCGTTCG, GACGCCCG, GACGCTCG, GACGTCCG, GACGTTCG, GGCGCCCG, GGCGCTCG, GGCGTCCG, GGCGTTCG, ATCGCCCG, ATCGCTCG, ATCGTCCG, ATCGTTCG, GTCGCCCG, GTCGCTCG, GTCGTCCG, and GTCGTTCG.

28. The method of claim 27, wherein the immunomodulatory nucleic acid molecule comprises the sequence AACGTTCG.

29. The method of claim 25, wherein the bacterium is *Mycobacterium tuberculosis*.

30. The method of claim 25, wherein the bacterium is *Mycobacterium avium*.

31. The method of claim 25, wherein the subject is immunocompromised.

32. The method of claim 31, wherein the sjeitunocompromised subject has a reduced number of CD4+ T cells relative to an immunocompetent subject.

33. A method treating a mycobacterial infection, the method comprising:

administering to a subject an amount of an immunomodulatory nucleic acid molecule in an amount effective to inhibit intracellular replication of a Mycobacterium bacterium in the subject, wherein the immunomodulatory nucleic acid comprises an immunostimulatory sequence comprising 5' CpG 3'; and administering to the subject an antimicrobial agent in an amount effective to decrease or inhibit growth of the Mycobacterium bacterium;

wherein said administering is effective to decrease severity of symptoms of disease caused by the Mycobacterium bacterium.

34. The method of claim 33, wherein the immunomodulatory nucleic acid molecule is administered in an amount effective to provide a synergistic, antimicrobial effect with the antimicrobial agent.

35. The method of claim 33, wherein the iimunomodulatory nucleic acid comprises a sequence selected from the group consisting of: AACGCC, AACGCT, AACGTC, AACGTT, AGCGCC, AGCGCT, AGCGTC, AGCGTT, GACGCC, GACGCT, GACGTC, GACGTT, GGCGCC, GGCGCT, GGCGTC, GGCGTT, ATCGCC, ATCGCT, ATCGTC, ATCGTT, GTCGCC, GTCGCT, GTCGTC, GTCGTT, TCGTCG, TCGTCGTCG, AACGCCCG, AACGCTCG, AACGTCCG, AACGTTCG, AGCGCCCG, AGCGCTCG, AGCGTCCG, AGCGTTCG, GACGCCCG, GACGCTCG, GACGTCCG, GACGTTCG, GGCGCCCG, GGCGCTCG, GGCGTCCG, GGCGTTCG, ATCGCCCG, ATCGCTCG, ATCGTCCG, ATCGTTCG, GTCGCCCG, GTCGCTCG, GTCGTCCG, and GTCGTTCG.

36. The method of claim 35, wherein the immunomodulatory nucleic acid comprises the sequence AACGTTCG.

37. The method of claim 33, wherein said administering of the immunomodulatory nucleic acid enhances indoleamine 2,3-dioxygenase activity in the subject.

38. The method of claim 1, wherein the anti-pathogenic agent is selected from the group consisting of clarithromycin, capreomycin sulfate; ethambutol HCl, isoniazid, aminosalicylic acid, rifapentine, pyrazinamide, rifampin, cycloserine, streptomycin sulfate, and ethionamide.

39. The method of claim 1, wherein the anti-pathogenic agent is rifampin and isoniazid in combination.

40. The method of claim 1, wherein the anti-pathogenic agent is rifampin, isoniazid, and pyrazinamide in combination.

41. The method of claim 33, wherein the anti-microbial agent is selected from the group consisting of clarithromycin, capreomycin sulfate; ethambutol HCl, isoniazid, aminosalicylic acid, rifapentine, pyrazinamide, rifampin, cycloserine, streptomycin sulfate, and ethionamide.

42. The method of claim 33, wherein the anti-microbial agent is rifampin and isoniazid in combination.

43. The method of claim 33, wherein the anti-microbial agent is rifampin, isoniazid, and pyrazinamide in combination.

* * * * *